US010271919B2

(12) United States Patent
Skroski et al.

(10) Patent No.: US 10,271,919 B2
(45) Date of Patent: Apr. 30, 2019

(54) BARRIER DISPENSER AND METHOD OF USING THE SAME

(71) Applicant: Sano Curatio, LLC, Henderson, NV (US)

(72) Inventors: Mitchell Edward Skroski, Asheville, NC (US); Richard Alan Swartzbaugh, Carlsbad, CA (US); Harvey Allan Bogarat, Temecula, CA (US); Barry Ray Hix, Birmingham, AL (US); Michael Douglas Plaut, Weston, VT (US); Norman Tien-Yo Chien, Sierra Madre, CA (US)

(73) Assignee: Sano Curatio, LLC, Henderson, NV (US)

( * ) Notice: Subject to any disclaimer, the term of this patent is extended or adjusted under 35 U.S.C. 154(b) by 0 days.

(21) Appl. No.: 15/636,483

(22) Filed: Jun. 28, 2017

(65) Prior Publication Data

US 2017/0367779 A1    Dec. 28, 2017

Related U.S. Application Data

(60) Provisional application No. 62/460,178, filed on Feb. 17, 2017, provisional application No. 62/436,105, (Continued)

(51) Int. Cl.
*A61B 50/30* (2016.01)
*A61B 90/00* (2016.01)
(Continued)

(52) U.S. Cl.
CPC .............. *A61B 50/30* (2016.02); *A61B 90/08* (2016.02); *A61B 7/00* (2013.01); *A61B 7/026* (2013.01);
(Continued)

(58) Field of Classification Search
CPC ......... A61B 50/30; A61B 90/08; A61B 46/10; A61B 7/026; A61B 2090/0813
(Continued)

(56) References Cited

U.S. PATENT DOCUMENTS 4,130,228 A * 12/1978 Perrin ................ B65D 83/0882
225/19
4,461,368 A    7/1984 Plourde
(Continued)

FOREIGN PATENT DOCUMENTS

EP        2238909 A1    10/2010
JP      2004329245 A    11/2004
(Continued)

OTHER PUBLICATIONS

International search report and written opinion dated Sep. 6, 2017 for PCT Application PCT-US2017039837.

*Primary Examiner* — Timothy R Waggoner
*Assistant Examiner* — Ayodeji T Ojofeitimi
(74) *Attorney, Agent, or Firm* — Wilson Sonsini Goodrich & Rosati

(57) ABSTRACT

Apparatus and methods for applying a barrier to a medical scope are provided. An apparatus may comprise a source of film and a housing. The housing may comprise a chamber configured to support therein the source of film, and an opening provided through a wall of the housing to permit a portion of the film to extend out of the chamber when the film is dispensed. The housing may comprise a recess located such that the extended portion of the film is permitted to hang freely in proximity to the recess. The recess may be sized to receive a distal portion of the medical scope. The recess may be adapted to allow the extended portion of the film to be applied to the distal portion of the medical scope
(Continued)

when the distal portion is placed into the recess with the portion of the film located therebetween.

20 Claims, 31 Drawing Sheets

Related U.S. Application Data filed on Dec. 19, 2016, provisional application No. 62/355,551, filed on Jun. 28, 2016.

(51) Int. Cl.
    *A61B 46/10*     (2016.01)
    *A61B 7/02*     (2006.01)
    *A61B 7/00*     (2006.01)

(52) U.S. Cl.
    CPC ....... *A61B 46/10* (2016.02); *A61B 2090/0813* (2016.02)

(58) Field of Classification Search
    USPC .......................................................... 181/131
    See application file for complete search history.

(56) References Cited

U.S. PATENT DOCUMENTS

| | | |
|---|---|---|
| 5,365,023 A | 11/1994 | Lawton |
| 5,424,495 A | 6/1995 | Wurzburger |
| 5,448,025 A | 9/1995 | Stark et al. |
| 5,466,897 A | 11/1995 | Ross et al. |
| 5,486,659 A | 1/1996 | Rosenbush |
| 5,528,004 A | 6/1996 | Wurzburger |
| 5,647,506 A | 7/1997 | Julius |
| 5,747,751 A | 5/1998 | Weckerle et al. |
| 5,798,489 A | 8/1998 | Gillio |
| 5,808,244 A | 9/1998 | Knight et al. |
| 5,813,992 A | 9/1998 | Henwood |
| 5,892,233 A | 4/1999 | Clement |
| 5,921,941 A | 7/1999 | Longobardo et al. |
| 5,949,032 A | 9/1999 | Wurzburger |
| 6,009,971 A | 1/2000 | Weidman et al. |
| 6,018,835 A | 2/2000 | Schonfeld |
| 6,019,187 A | 2/2000 | Appavu |
| 6,206,134 B1* | 3/2001 | Stark ........................ A61B 7/02 |
| | | 181/131 |
| 6,467,568 B1 | 10/2002 | Kemper |
| 6,499,560 B1 | 12/2002 | Lang et al. |
| 6,520,281 B1 | 2/2003 | Deslauriers et al. |
| 6,575,917 B2 | 6/2003 | Giroux et al. |
| 7,117,971 B1* | 10/2006 | Cornacchia ............. A61B 7/02 |
| | | 181/131 |
| 7,360,625 B2 | 4/2008 | Stickley |
| 7,424,929 B1 | 9/2008 | Martinez |
| 7,705,325 B2 | 4/2010 | Vestal |
| 7,712,575 B1 | 5/2010 | Moore |
| 7,757,807 B1 | 7/2010 | Martinez |
| D621,504 S | 8/2010 | Martinez |
| 7,823,690 B2 | 11/2010 | Hirsch et al. |
| 7,891,462 B2 | 2/2011 | Hmayakyan et al. |
| 7,921,959 B2 | 4/2011 | Statner et al. |
| 7,942,597 B2 | 5/2011 | Perlman et al. |
| 8,025,120 B2 | 9/2011 | Eddy |
| 8,042,646 B2 | 10/2011 | Gross |
| 8,057,117 B2 | 11/2011 | Perlman et al. |
| 8,387,745 B2 | 3/2013 | Gross |
| 8,393,818 B2 | 3/2013 | Perlman et al. |
| 8,779,385 B2 | 7/2014 | Noori |
| 8,985,267 B2 | 3/2015 | Fishberger et al. |
| 9,486,287 B2 | 11/2016 | Beebe et al. |
| 9,561,079 B2 | 2/2017 | Perlman et al. |
| 2002/0170771 A1 | 11/2002 | Milam et al. |
| 2005/0092765 A1 | 5/2005 | Chasid et al. |
| 2006/0076184 A1 | 4/2006 | Robinson |
| 2006/0147339 A1 | 7/2006 | Hunter et al. |
| 2006/0213920 A1 | 9/2006 | Agarwal et al. |
| 2007/0045039 A1 | 3/2007 | Agahi et al. |
| 2008/0166384 A1 | 7/2008 | Jones |
| 2008/0223867 A1 | 9/2008 | Carr |
| 2008/0230303 A1 | 9/2008 | Weidman |
| 2008/0251313 A1 | 10/2008 | Knight et al. |
| 2010/0116841 A1* | 5/2010 | Perlman ................... A61L 2/18 |
| | | 221/222 |
| 2010/0326850 A1 | 12/2010 | Manlapaz |
| 2011/0186590 A1* | 8/2011 | Lee ........................ A61B 50/30 |
| | | 221/73 |
| 2012/0051969 A1 | 3/2012 | Nahman et al. |
| 2012/0261593 A1* | 10/2012 | Noori ....................... A61L 2/10 |
| | | 250/492.1 |
| 2012/0318606 A1 | 12/2012 | Wang |
| 2013/0108507 A1 | 5/2013 | Reiseneder et al. |
| 2013/0341223 A1* | 12/2013 | Fong ........................ A61B 7/02 |
| | | 206/363 |
| 2014/0319000 A1 | 10/2014 | Fishberger et al. |
| 2015/0014348 A1 | 1/2015 | Tedesco et al. |
| 2015/0327933 A1 | 11/2015 | Perlman |
| 2016/0000508 A1 | 1/2016 | Finn |
| 2016/0045266 A1 | 2/2016 | Deporto et al. |
| 2016/0296199 A1 | 10/2016 | Mukherjee et al. |
| 2016/0338790 A1 | 11/2016 | Krupnick |
| 2017/0020618 A1 | 1/2017 | Lakes |
| 2017/0053076 A1 | 2/2017 | Lulla et al. |

FOREIGN PATENT DOCUMENTS

| | | |
|---|---|---|
| KR | 20170002815 A | 1/2017 |
| WO | WO-2009151583 A1 | 12/2009 |
| WO | WO-2010031151 A1 | 3/2010 |
| WO | WO-2014186362 A1 | 11/2014 |
| WO | WO-2014204518 A2 | 12/2014 |
| WO | WO-2018005703 A1 | 1/2018 |

* cited by examiner

BARRIER DISPENSER AND METHOD OF USING THE SAME

CROSS-REFERENCE

This application claims the benefit of U.S. Provisional Patent Application No. 62/355,551 filed Jun. 28, 2016; U.S. Provisional Patent Application No. 62/436,105 filed Dec. 19, 2016; and U.S. Provisional Patent Application No. 62/460,178 filed Feb. 17, 2017, which applications are incorporated herein by reference in their entireties for all purposes.

BACKGROUND

Hospital-acquired infections (HAIs) pose a real and monumental threat to the health and life of patients across the healthcare continuum, including acute care hospitals, skilled nursing facilities, and outpatient environments such as primary care physician (PCP) & specialty hospital clinics, surgery centers, occupational health clinics, and physician offices. HAIs are generally acquired from acute & post-acute settings. The Centers for Disease Control and Prevention recognize that hospital-acquired infections (HAIs) are one of the major challenges in US hospitals. Transmission of contaminants typically occurs in one out of every 32 patient encounters, and healthcare personnel (doctors, nurses, etc.) are required to clean stethoscopes between patients for 60 seconds. However, studies have shown that more than 95% of healthcare personnel may be non-compliant with the above practice. Thus, a significant need exists for protection from contaminated stethoscopes, which is one of the major contributors to the risk of HAIs to both patients and healthcare personnel.

SUMMARY

Apparatus and methods for applying protective barriers to medical scopes are provided herein. A medical scope as described herein may include a stethoscope, and may be interchangeably referred to herein as a stethoscope, medical scope, scope, or scopes. The apparatus and methods can be used with scopes of various shapes and/or sizes, and with different types of scopes such as adult stethoscopes and pediatric stethoscopes. The barrier can be used to reduce or eliminate contamination to a stethoscope head or drum, and may be interchangeably referred to herein as film, or proprietary membrane. The barrier can be used to reduce the risk of microbial, bacterial, viral, disease, or pathogenic transmissions between patients and/or users. The barrier can be an antimicrobial, antiviral, antipathogenic, or antibacterial barrier. The barrier can serve as an antimicrobial, antiviral, antipathogenic, or antibacterial barrier for the stethoscope head. The barrier may include an antimicrobial, antiviral, antipathogenic, or antibacterial substance that can neutralize or destroy microbes, organic matter, contain disinfectants, metals, or a combination of both. The barrier can help to reduce or eliminate contamination of the stethoscope head when the stethoscope is being used on multiple patients. The risk of hospital-acquired infections (HAIs) to patients and users (e.g. healthcare personnel) can be significantly reduced, through use of the protective barrier applied using the apparatus and methods described herein. The barrier may be branded by a client utilizing their logo, trademark, "Doing Business As" (DBA), company name, product name, or stock keeping unit (SKU).

According to some aspects of the invention, an apparatus for dispensing a film for use with a medical scope is provided. The apparatus may include a source of film and a housing. The housing may include a chamber configured to receive and support therein the source of film. The housing may also include an opening provided through a wall of the housing, wherein the opening is configured to permit a portion of the film to extend out of the chamber from the opening when the film is dispensed. The housing may also include a cover so that no film is exposed until use. The housing may further include a recess provided on the housing and located such that the extended portion of the film is permitted to hang freely in proximity to the recess. Some portions of the film may be affixed using fingertips. The recess is sized to receive a distal portion of the medical scope. The recess is adapted to allow the extended portion of the film to be applied to the distal portion of the medical scope when said distal portion is placed into the recess with the portion of the film located therebetween.

The device may be mounted utilizing an adhesive, screws, or otherwise vertically affixed to a wall, cubicle, medication cart, nurses' office, inside an ambulance, or any other vertical surface accessible to health care professionals.

Further aspects of the invention provide a method for dispensing a film for use with a medical scope. The method may include providing an apparatus for dispensing the film, wherein the apparatus comprises a chamber configured to receive and support therein a source of film. The method may also include dispensing a portion of the film from an opening provided through a wall of the housing; extending the portion of the film such that the extended portion hangs freely over a recess provided on the housing, wherein the recess is sized to receive a distal portion of the medical scope; placing the distal portion of the medical scope into the recess with the extended portion of the film located therebetween; and applying the extended portion of the film to the distal portion of the medical scope. Some portions of the film may be affixed using fingertips. The method may also include dispensing a portion of the film from an opening provided through a wall of the housing; extending the portion of the film such that the extended portion is suspended over a covered recess provided on the housing, wherein the recess is sized to receive a distal portion of a stethoscope; placing the distal portion of the stethoscope into the recess with the extended portion of the film located therebetween; and applying the extended portion of the film to the distal portion of the stethoscope. Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 9 through 17 are perspective views showing application of the barrier to the stethoscope head in accordance with the method shown in FIGS. 8A-8F;

FIG. 9 is a perspective view showing a film dispensed from the opening of the dispenser;

FIG. 10 is a perspective view showing a stethoscope head being placed onto the portion of the film in front of the recess;

FIG. 11 is a perspective view showing the stethoscope head being moved from a center of the recess to a first rounded concave lobe;

FIG. 12 is a perspective view showing the stethoscope head being moved from the first rounded concave lobe to a second rounded concave lobe within the recess;

FIG. 13 is a perspective view showing the stethoscope head being moved from the second rounded concave lobe to a third rounded concave lobe within the recess;

FIG. 14 is a perspective view showing the stethoscope head being moved from the third rounded concave lobe back to the first rounded concave lobe within the recess;

FIG. 15 is a perspective view showing the stethoscope head and the film being pulled downwards until the stethoscope head is below the cutting edge;

FIG. 17 is a perspective view showing the barrier as applied to the stethoscope head;

DETAILED DESCRIPTION

Figure 1A:
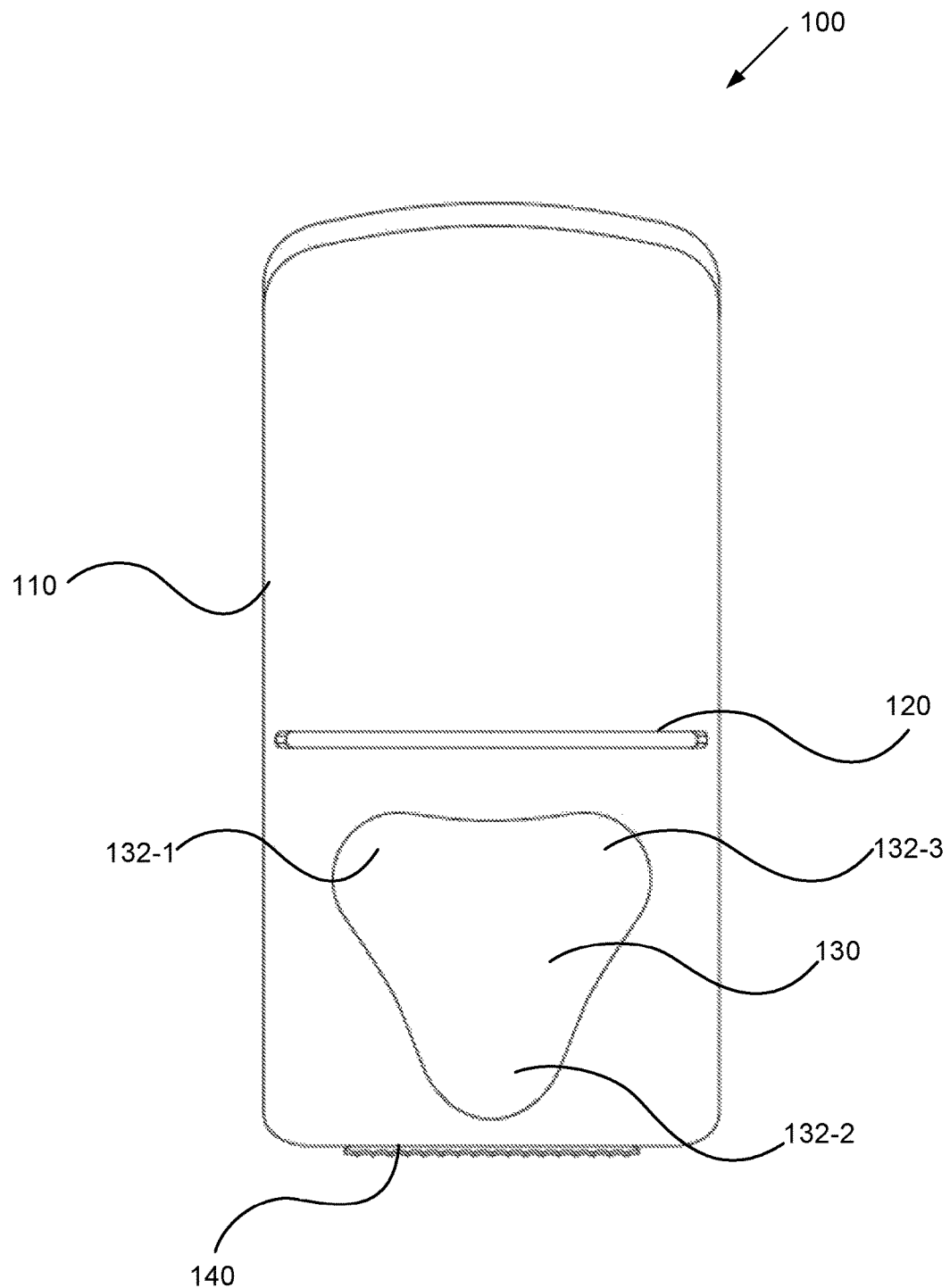
FIG. 1A is a front view of a barrier dispenser in accordance with an embodiment.

While preferred embodiments of the present invention have been shown and described herein, it will be appreciated by those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope of the invention and that methods and structures within the scope of these claims and their equivalents be covered thereby.

The invention provides apparatus and methods for applying a barrier to medical scopes, for example to the drum or head of a stethoscope. The drum or head of the stethoscope may include one or more acoustic sensors. The stethoscope head may be configured to be placed onto a patient's body. The apparatus and methods disclosed herein can be used with scopes of various shapes and/or sizes, and with different types of scopes such as adult stethoscopes and pediatric stethoscopes. The barrier can be an antimicrobial, antiviral, antipathogenic or antibacterial. The barrier can serve as an antimicrobial, antiviral, antipathogenic or antibacterial barrier for the stethoscope head. The barrier may include an antimicrobial, antiviral, antipathogenic or antibacterial substance that can neutralize or destroy microbes, organic matter, contain disinfectants, metals, or a combination of both. The barrier can help to reduce or eliminate contamination of the stethoscope head when the stethoscope is being used on multiple patients. The risk of hospital-acquired infections (HAIs) to patients and healthcare personnel can be significantly reduced, through use of the protective barrier applied using the apparatus and methods described herein. Additionally, the invention does not require complex mechanical systems to apply the barrier, thereby reducing manufacturing, assembly and parts costs. In some cases, the cost of the apparatus and the barrier can be less than $0.25 per use, and can provide an economical solution compared to the use of disinfecting solutions (e.g., for killing pathogens such methicillin-resistant *Staphylococcus aureus* (MRSA) or *C Diff Clostridium difficile*) which generally cost more per unit/gallon. The disclosed apparatus and methods are reliable, robust and can be used for multiple patient encounters over extended periods of time. The apparatus can also be easily assembled and disassembled, and can be used with various types of barrier materials provided in different forms such as films, membranes, rolls, stacked sheets, perforated sheets, wraps, cassette dispensers, etc.

The apparatus and methods disclosed herein provide a sanitary way of applying a barrier to a stethoscope head, thereby reducing or eliminating human contact during application of the barrier. This can help to address the issue of poor stethoscope hygiene. Accordingly, exposure to microbial, viral, pathogenic or bacterial contaminants between patients and healthcare personnel can be largely eliminated, mitigated, or reduced properly using the apparatus, methods, and protocols described herein.

Various aspects of the invention described herein may be applied to any of the particular applications set forth below and for any other types of scopes in addition to stethoscopes. The invention may be used in any system that requires application of a protective barrier to an object. The invention may be applied as a standalone apparatus or method, or as part of a medical system in a healthcare environment. It shall be understood that different aspects of the invention can be appreciated individually, collectively, or in combination with each other.

FIG. 1A is a front view of a barrier dispenser 100 in accordance with an embodiment. A barrier dispenser as described herein may refer to any apparatus, device or system that is designed, configured, or used for applying a barrier to a medical scope such as a stethoscope. The barrier can serve as a protective barrier or shield for the head or drum of the stethoscope. The dispenser can be configured to apply a barrier onto a variety of stethoscopes including adult care stethoscopes, pediatric stethoscopes, cardiology stethoscopes, electronic stethoscopes, Emergency Medical Technicians (EMT)/Emergency Medical Services (EMS) stethoscopes, anesthesiologist stethoscopes, and the like. The dispenser can be used to apply the barrier onto the stethoscopes for different applications including adult cardiac diagnoses, pediatric diagnoses, etc. The dispenser and the barrier can be used in a variety of environments including hospitals, clinics, emergency rooms, patient examination rooms, acute care patient rooms, ambulatory care, pediatrics, field environments, nurse's offices in educational settings, occupational health clinics, surgery or operation rooms, places that pose high risk of infection from microbes, viruses, pathogens, germs, diseases, bacteria, etc. The barrier is designed such that it does not interfere with the acoustic detection of the stethoscope. For example, the barrier may be a thin membrane that allows acoustic signals from the body to be transmitted through in an unimpeded manner. The barrier is disposable and designed for use in a single patient encounter.

The dispenser can be used to apply a barrier to the stethoscope head prior to the stethoscope head contacting the patient's body, so as to reduce or prevent contamination of the stethoscope head or risk of infection to the patient. The barrier may be a thin film or a membrane, and may be made of a polymer such as polyurethane, or any other medical-grade or food-grade plastics. The film may be latex free. The film may include antimicrobial, antiviral, germicidal, antipathogenic, and/or bactericidal properties. The film may or may not include silver, copper, titanium, other metals, formulas, or compounds. The film may also include any other antimicrobial formula, property, surface, or agent that is designed to help reduce concentrations of microbes, viruses, germs, pathogens, microorganisms, disease, or bacteria on the stethoscope head.

The dispenser can include biologically acceptable materials suitable for medical applications, depending on the particular application and/or preference of a medical practitioner. For example, components of the dispenser can include or be fabricated from materials such as cellophane, vinyl, acetate, polyethylene acrylic, butyl rubber, ethylene-vinyl acetate, natural rubber, a nitrile, silicone rubber, a styrene block copolymer, a vinyl ether, or a tackifier. Antimicrobial and/or antiseptic materials include but are not limited to: sodium bicarbonate; hydrogen peroxide; benzalkonium chloride; chlorohexidine; hexachlorophene; iodine compounds; and combinations thereof. In some embodiments, the antimicrobial and/or antiseptic materials may not include alcohols (such as ethanol, 1-propanol and 2-propanol/isopropanol or mixtures of these alcohols), since solvents/alcohols may promote the airborne transmission of certain types of micro-organisms, and certain type of microbes may be resistant to alcohols. For example, certain types of microorganisms (e.g., *Clostridium Difficile* (*C. Diff*)) can cause spores and facilitate airborne transmission when interacting with solvents.

Antimicrobial materials can further include but are not limited to: beta-lactam antibiotics (such as penicillin, cephalosporin); protein synthesis inhibitors (such as aminoglycosides, macrolides, tetracycline, chloramphenicol, polypeptides); sulphonamides; cotrimoxazole; quinolones; anti-viral agents; anti-fungal agents; anti-cancer drugs; anti-malarial drugs; anti-tuberculosis drugs; anti-leprotic drugs; anti-protozoal drugs and combinations thereof.

An antimicrobial material may include, for example, a silver-based antimicrobial material, a copper-based antimicrobial material, a titanium-based antimicrobial material, chlorhexidene gluconate, benzalkonium chloride, a mono-quaternary and/or polyquaternary ammonium salt-based antimicrobial material, a biguanide-based antimicrobial such as polyhexamethylene biguanide, triclosan, zinc pyridine, an isothiazolinone-based antimicrobial, a 10,10'-oxy-bisphenoxarsine-based antimicrobial, a peptide-based antimicrobial, a natural antimicrobial such as hops extract, honey, a chitosan-based antimicrobial, and combinations thereof.

Optionally in any of the embodiments disclosed herein, one or more components of the dispenser can include or be fabricated from materials such as polyvinyl chloride, polyvinylidene chloride, low density polyethylene, linear low density polyethylene, polyisobutene, poly[ethylene-vinylacetate] copolymer, lightweight aluminum foil and combinations thereof, stainless steel alloys, commercially pure titanium, titanium alloys, silver alloys, copper alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of the dispenser may have material composites, including one or more of the above materials, to achieve various desired characteristics such as strength, rigidity, elasticity, compliance, biomechanical performance, durability and/or radiolucency preference. One or more of the components of the dispenser may comprise antimicrobial and/or antiseptic materials. The components of the dispenser, individually or collectively, may also be fabricated from a heterogeneous material such as a combination of two or more of the above-described materials. The components of the dispenser may be monolithically formed or integrally connected.

It is well-known in the art that certain forms of electromagnetic energy, such as UV light and specifically UV-C, has potent germicidal properties. Optionally, the present disclosure provides methods for sterilizing or disinfecting a film or barrier, including: exposing the film or the barrier to electromagnetic energy having a wavelength preferably between about 100 nm and about 280 nm, more preferably between about 200 nm-280 nm, or even more preferably between about 240 nm-270 nm, where the exposure may result in sanitization or disinfection of the film or barrier, or even sterilization of the film or barrier depending on how much UV energy is applied to the film or barrier.

The barrier that is applied a stethoscope head may be optically translucent, transparent, or branded by client utilizing their logo, trademark, "Doing Business As" (DBA), company name, product name, or stock keeping unit (SKU). Alternatively, the barrier may be opaque. The barrier/film may have tensile strength of ranging from about 5 to 30 lbs/in, and an elongation ranging from about 110% to 240%. The barrier may include an anti-microbial, antiviral, antipathogenic, or antibacterial material for reducing the amount of microbes, viruses, pathogens, germs, diseases, or bacteria on the stethoscope head before patient use. The barrier protects the healthcare professional and patient. The antimicrobial, antiviral, germicidal, antipathogenic, and/or bactericidal properties may be pre-fabricated into the film/barrier. The antimicrobial, antiviral, germicidal, antipathogenic, and/or bactericidal properties may also be applied to the barrier. For example, the anti-microbial material may be coated or sprayed onto the barrier after the barrier has been applied onto the stethoscope head. Optionally in any of the embodiments disclosed herein, UV/UV-C may also be applied to the barrier, barrier roll, barrier cassette, or individual barrier sheets. The barrier may include an adhesive for detachably attaching the barrier to the stethoscope head. The adhesive may be a weak adhesive that preferably does not leave a residue on the stethoscope head when removed therefrom. The adhesive may have an adhesion strength that prevents the barrier from peeling or falling off the stethoscope head during use with a patient, but that allows the barrier to be easily and manually removed from the stethoscope head after use (for disposal). Optionally in any of the embodiments disclosed herein, the adhesive may an adhesive or peel strength ranging from about 1 to 20 oz/in. The barrier may comprise a material that is acoustically transmissive and substantially impermeable to microorganisms and fluids. Optionally in any of the embodiments disclosed herein, the barrier may comprise polyvinyl chloride, polyvinylidene chloride, low density polyethylene, linear low density polyethylene, polyisobutene, polyethylene-vinylacetate copolymer, lightweight aluminum foil and combinations thereof.

The dispenser may be rigidly or detachably mounted to any structure. For example, the dispenser can be mounted to the wall of a hospital room, edge of a table, side of a medication cart, interior wall of a medical transport vehicle, cube wall, or any other appropriate vertical surface. The dispenser can also be mounted to a vehicle, for example within a compartment or sidewall of an ambulance or emergency vehicle. Alternatively, a portable, single-use dispenser can be stand-alone and need not be mounted onto any object. In some cases, the dispenser may be worn or carried by a user, for example on a lab coat, pocket, purse, or on the hip. The dispenser may be portable and configured for use in a variety of environments or applications as described herein.

Referring to FIG. 1A, the dispenser 100 may include a housing 110. The housing may be formed having any shape and/or size. The housing can be configured to support a source of barrier material (e.g. a roll of film, a cassette of film, or individual sheets of film) as described elsewhere herein. Optionally in any of the embodiments disclosed herein, the housing may be a substantially rectangular plastic hollow box. The housing may be, for example approximately 6 inches wide, approximately 9 inches long, and 3-6 inches deep. The housing may be configured for mounting on a vertical surface such as, for example, a wall of a room, cube wall, interior of a medical transport, medication cart. Optionally in any of the embodiments disclosed herein, a bracket may be provided that allows the housing to be mounted directly to the vertical surface. The housing may engage the bracket in a manner that affixes the housing relative to the vertical surface. The housing may be formed using any number of techniques known in the art such as injection molding, blow molding, three-dimensional (3D) printing, etc.

The housing may include a chamber (not shown). The chamber may be configured to receive and support a source of barrier material. The barrier material may include a film or membrane. Optionally in any of the embodiments disclosed herein, the source may include a source of film for use with a medical scope. The film may have a thickness ranging from about 10 μm to about 1000 μm. For example, the film may have preferably have a thickness from about 10 μm to about 200 μm, and most preferably from about 20 μm to about 30 μm. In some cases, the film may have a thickness less than 10 µm or greater than 1000 µm. Optionally in any of the embodiments disclosed herein, the film may have a thickness of about 1 mil. The dispenser can be configured to dispense the film to form a barrier on the stethoscope head (using the healthcare professional's gloved hand.) The barrier can be formed by covering the stethoscope head with the film as described later herein. An opening 120 may be provided through a wall of the housing. The opening may be a through-hole that provides access between the chamber of the housing and an external environment. The opening can permit the film to extend out of the chamber when the film is being dispensed. In the example of FIG. 1A, the opening is formed as a slot although the invention is not limited thereto. The opening can be formed having any shape and/or size to accommodate the dimensions of the film and to allow the film to pass through but preferably is sized to accommodate the film width and thickness to allow the film to pass through the slot while minimizing the slot opening thereby helping to prevent dust, particles or other contaminants from entering the housing. In one or more of the embodiments described herein, the opening may be formed having a circular or elliptical shape, and configured to permit separate sheets to be dispensed from a plurality of interleaved stacked sheets.

The housing 100 may further include a recess 130. The recess may be provided on a wall of the housing. As shown in FIG. 1A, the recess is located below the opening although the invention is not limited thereto. In some cases, the recess can be located above the opening or anywhere on the housing. The recess may be formed having any shape, design, depth, and/or size. Examples of possible shapes or designs include but are not limited to: mathematical shapes, two-dimensional geometric shapes, multi-dimensional geometric shapes, curves, polygons, polyhedral, polytopes, minimal surfaces, ruled surfaces, non-orientable surfaces, quadrics, pseudospherical surfaces, algebraic surfaces, miscellaneous surfaces, riemann surfaces, box-drawing characters, cuisenaire rods, geometric shapes, shapes with metaphorical names, symbols, unicode geometric shapes, shapes based on math symbols characters from any language history music art science religion, or any other form. Optionally in any of the embodiments disclosed herein, the recess may have a substantially circular or elliptical shape.

In the example of FIG. 1A, the recess 130 may have a substantially triangular shape, or any other shape. The recess may be symmetrical, for example an equilateral triangle. Alternatively, the recess may have an irregular shape and need not be symmetrical. The recess may have rounded corners. For example, each corner of the recess may be rounded having a radius in a range from about 5 mm to about 50 mm. In some cases, the radius of the corner may be less than 5 mm or greater than 50 mm. Optionally in any of the embodiments disclosed herein, each corner of the recess may include rounded concave lobe. For example, in FIG. 1A, the recess may include a plurality of rounded concave lobes 132 forming the triangular shaped recess. A first lobe 132-1 may be located at the top left corner of the recess, a second lobe 132-2 may be located at the bottom corner of the recess, and a third lobe 132-3 may be located at the top right corner of the recess. The recess may include any number of rounded concave lobes.

The recess 130 can be sized and/or shaped to receive a distal portion of a medical scope, for example the head or drum of a stethoscope. The recess may be formed as a sunken cavity or trench on the wall of the housing. In some cases, the recess may be formed as a molded extrusion into the chamber of the housing. The recess may have a depth ranging from about 2 mm to about 10 mm, or preferably at least deep enough to receive the head or drum of the stethoscope. In some cases, the recess may have a depth that is less than 2 mm or greater than 10 mm.

Optionally in any of the embodiments disclosed herein, the recess may be coated or sprayed with a copper, silver, titanium or other metal, coating, or any other antimicrobial material, anti-viral material, surfactants or agents that are designed to reduce microorganisms, disease, virus, cellular, bacteria, or airborne or surface particulates from clinging onto the surface and/or edges of the recess. Optionally in any of the embodiments disclosed herein, one or more walls of the recess may be impregnated with an antimicrobial material. For example, the antimicrobial material may be integrally formed with the recess of the housing to help control the bacterial level present on or within the recess.

The dispenser may optionally include a cutting edge. For example, FIG. 1A shows a cutting edge 140 located on a bottom portion of the housing 110. A sliding cutter may also be included. The cutting edge may be detachably coupled to the housing, or integrally formed as part of the housing. The cutting edge can include a serrated sharp edge or it may simply be a sharp edge that is used to cut and release a portion of the film after the barrier has been applied to a stethoscope head.

Optionally in any of the embodiments disclosed herein, the dispenser need not include a cutting edge. For example, the film may be segmented into a plurality of pieces that are separably coupled together by perforations. The plurality of pieces may include any number of pieces, for example 100, 200, 300, 400, 500, 600, 700, 800, 900, 1000, 2500, greater than 2500, or any number in-between. The perforations allow each piece to be manually separated from the rest of the roll for a single use with the stethoscope. Alternatively, each piece or sheet may be stacked individually and interleaved together, for example similar to interleaved stacked tissue sheets (e.g. Kleenex®). Each piece may be used to form a barrier on the stethoscope head. Accordingly, a cutting edge, or a rolling cutter can be omitted in those embodiments since the pieces of film can be manually and easily separated by hand along the perforations, and are separate and distinct sheets of barrier.

Figure 1B:
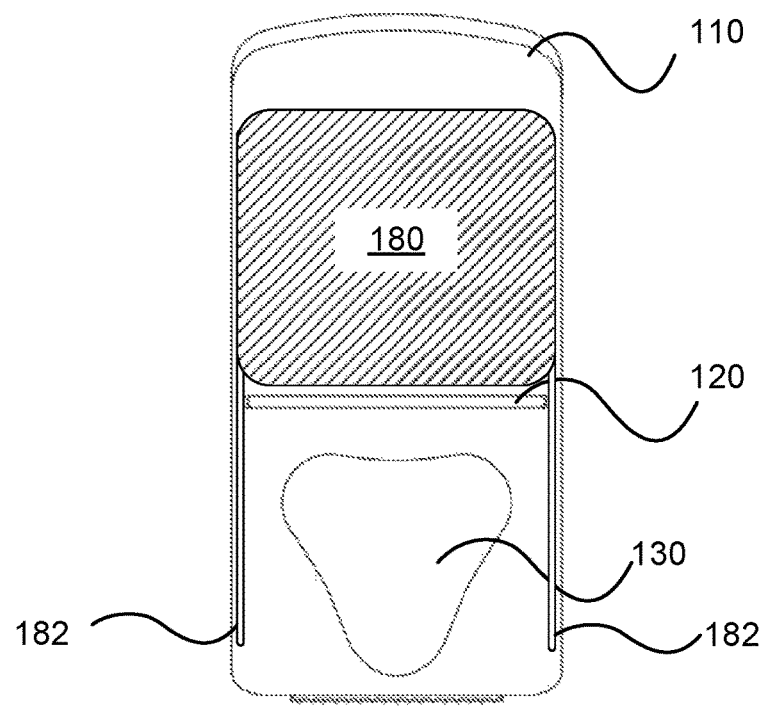
FIGS. 1B and 1C are front views of a barrier dispenser comprising a cover in accordance with an embodiment.
Figure 1C:
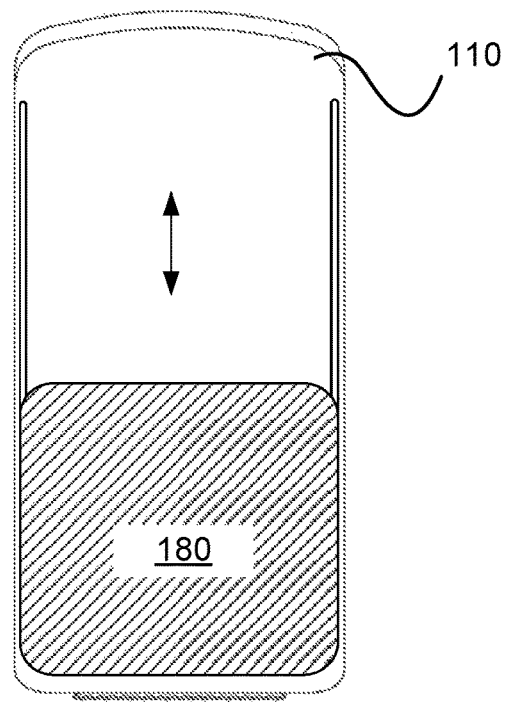

Optionally in any of the embodiments described herein, a cover may be provided on the housing. For example, FIGS. 1B and 1C show front views of a barrier dispenser comprising a cover 180. The cover may be located on the front portion of the housing 110, or anywhere on the housing. The cover may be configured to cover the opening 120 and the recess 130 when the dispenser is not in use, so as to protect the recess and the barrier material within the housing from microbes, viruses, germs, pathogens, microorganisms, disease, or bacteria possibly transmitted airborne or via human contact. The cover may be moved to an open position to permit access to the opening 120 and the recess 130 when the dispenser is in use or to be used. The cover can be movable, for example with the aid of a sliding mechanism 182. The sliding mechanism may include rails, bearings, wheels, dovetail designs, belts, chains, rack and pinion, or any combination thereof. The cover may be manually opened or closed by a user sliding the cover between an open position (FIG. 1B) and a closed position (FIG. 1C). The sliding motion may include translation along a vertical axis. Optionally in any of the embodiments described herein, the cover may be opened or closed via a combination of translation and/or rotation motions. Optionally in any of the embodiments described herein, the cover may be configured to automatically open or close in response to an input from an operator, for example via switches, actuators, motion detection sensors, etc.

Figure 2A:
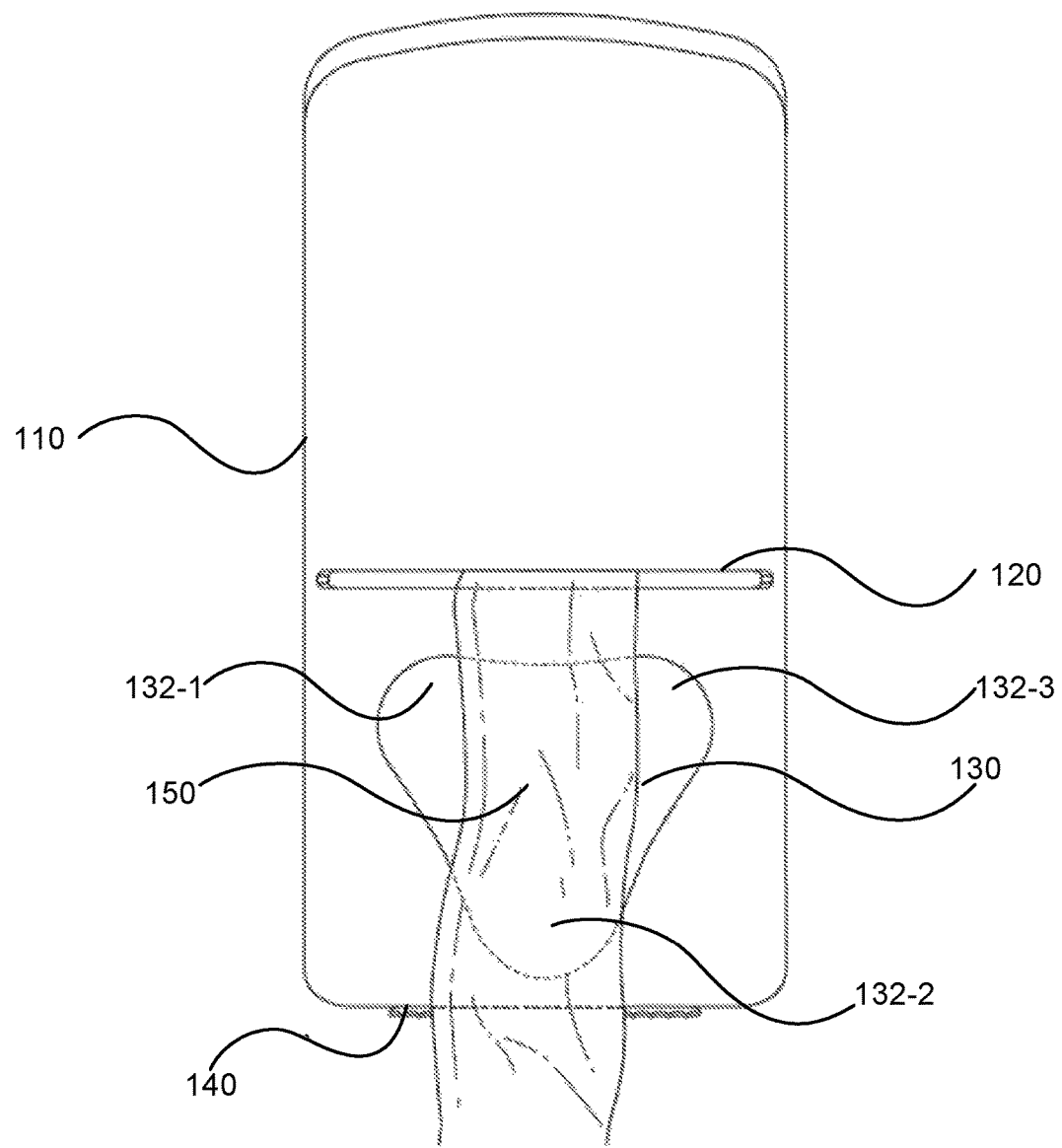
FIG. 2A is a front view of the dispenser of FIG. 1A and shows a film hanging in proximity to a recess.

FIG. 2A is a front view of the barrier dispenser from FIG. 1A showing a film hanging in proximity to a recess. The recess 130 may be located such that a film 150 is permitted to hang freely in proximity to the recess. The film may be dispensed from the opening 120 to hang or drape freely over the recess. Prior to use, an operator may remove a hanging piece of film, pull out a fresh or new piece of film, and proceed with applying the fresh or new piece of film to the stethoscope head. The film may be provided as a roll of film, cassette, or individual stacked sheets of film supported within the chamber of the housing 110. The roll of film, cassette, or individual stacked sheets of film may contain sufficient film for applying a plurality of barriers onto the stethoscope head for a large number of patient encounters (for example, tens, hundreds or thousands of patients). The dispenser may be configured to dispense the film from the opening, in a manner similar to paper towel dispensers that are used in public restrooms. The dispenser may include a mechanism for a user to manually dispense the film (for example by cranking a bar or turning a knob on the housing). Alternatively, the dispenser may be configured to automatically dispense a predetermined amount of film to form a single barrier for each use or patient encounter.

As shown in FIG. 2A, the film 150 may be dispensed such that it hangs directly in front of the recess. The film may drape over the recess. The film may or may not completely cover the recess. In the example of FIG. 2A, the film may extend over the recess covering only the second lobe 132-2 at the bottom corner of the recess. The first lobe 132-1 and third lobe 132-3 at the top left and right corners of the recess may not be covered by the film. Optionally in any of the embodiments disclosed herein, the film may drape over the recess completely covering the first, second and third lobes as described and illustrated elsewhere herein.

The recess 130 can be adapted to allow the film 150 to be applied to a stethoscope head when the stethoscope head is placed into the recess with the film located in-between. For example, a user can place the stethoscope head onto the overhanging film and into the recess, and move the stethoscope head within the recess to apply the film to the stethoscope head to form the barrier. The radius of the corners and/or the rounded concave lobes can be adapted to receive different stethoscope heads having different dimensions (e.g. diameter or thickness). The radius of the corners and/or the lobes can be adapted to allow the film to conform or wrap around the stethoscope head, when the stethoscope head is moved within the recess between the corners and/or the rounded concave lobes. The radius of the corners and/or the lobes can be configured to permit a user to slide the stethoscope head in a smooth manner from a first position to a second position within the recess thereby securing the film to the scope. Exemplary methods of forming or applying the barrier to the stethoscope head will be described in more detail elsewhere herein.

The recess 130 may have a larger size than the stethoscope head in order to permit translation and/or rotation of the stethoscope head within the recess. Optionally in any of the embodiments disclosed herein, the size of the recess may be greater than the size of the stethoscope head by at least about 5%, 10%, 15%, 20%, 25%, 30%, 35%, 40%, 45%, or 50%. The size of the recess may be defined by one or more dimensions of the recess, e.g. diameter, circumference, diagonal, length, width, height, thickness, area, volume, distance between two or more arbitrary points, etc. The size of the stethoscope head may be defined in a similar manner, for example based on its width, diameter and/or thickness. The stethoscope heads may have different shapes and/or sizes, and can be configured for different uses (e.g. adult, pediatric, etc.) as previously described. The recess can be configured to receive stethoscope heads of different shapes and/or sizes, and stethoscopes for different applications (e.g. adult, pediatric, EMS, etc.) as described elsewhere herein. As an example, the recess can be configured to receive stethoscope heads of different diameters, thicknesses, and/or form factors. Optionally in any of the embodiments disclosed herein, a width of the recess may range from about 2 to 6 inches. Alternatively, the width of the recess may be less than 2 inches or greater than 6 inches.

The bottom of the recess may be substantially planar to permit in-plane movement of the stethoscope head within the recess. The bottom of the recess may be configured to be substantially planar if the stethoscope head has a substantially planar surface at its distal end. Optionally in any of the embodiments disclosed herein, a surface profile at the bottom of the recess can be configured or designed to match the distal surface of the stethoscope head. For example, if the stethoscope head has a slight convex profile at its distal end, the bottom of the recess may be slightly concaved to increase contact area between the two. Increased contact area allows the film to be sufficiently and evenly applied over the distal surface of the stethoscope head, with reduced airgaps or creases in-between, thereby forming a well-adhered protective barrier.

The recess may include a surface at its bottom on which the stethoscope head (and film) is configured to move. Essentially, any conceivable material may be employed in forming the surface of the recess. The surface of the recess may be made of metals, plastics, composites, glass, organic materials, inorganic materials, or a combination of any of these. The surface of the recess may have any convenient shape, such as a curved shape, spherical, hemispherical, square, circle, cuboid, trapezoidal, disc, etc. The surface of the recess may be smooth, or may take on a variety of alternative surface configurations. For example, in some cases, the surface of the recess may contain raised or depressed regions. In some cases, the surface of the recess may include plates, sheets, pads, slices, films, slides, bearing layers, etc. In some cases, tracks can be formed on the surface of the recess. By way of example, the tracks may include grooves, trenches, mesa structures, or the like. The stethoscope head can be configured to move along the tracks on the surface of the recess. The surface of the recess may comprise a number of discrete pieces arranged together leaving gaps therebetween to form the tracks. Alternatively, the tracks may be machined or etched onto the surface of the recess using well-known techniques to provide for desired surface features. For example, machining processes such as milling, laser cutting, water jets, etc. can be employed in the formation of the tracks on the surface of the recess.

Optionally in any of the embodiments disclosed herein, the bottom of the recess may include a material that has a lower adhesion strength/affinity to the film than to the stethoscope head. This ensures that the film does not adhere to the bottom of the recess when the stethoscope head is placed into the recess, moved within the recess, or removed from the recess. In some cases, the bottom of the recess may be sprayed or coated with a material having non-stick properties that prevents the film from sticking or adhering to the bottom of the recess.

The bottom of the recess may have a rigid surface that does not deform when the stethoscope head is pressed into and moved within the recess. Alternatively, the bottom of the recess may include an elastic material such as an elastomer. The elastic material may be configured to conform to the shape of the stethoscope head. The elastic material may compress or press the film against the stethoscope head when the stethoscope head is placed into or moved within the recess. The compression may help to improve the contact area between the film and the stethoscope head. As described above, increased contact area allows the film to be sufficiently applied over the distal end of the stethoscope head, with reduced airgaps or creases in-between, thereby forming a well-adhered protective barrier.

Figure 2B:
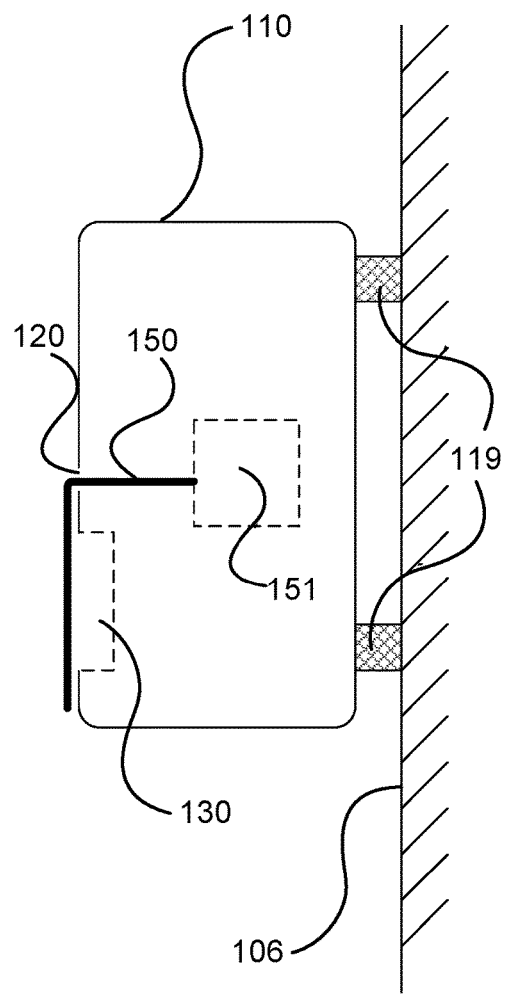
FIG. 2B is a schematic cross-sectional side view of the dispenser of FIG. 2A mounted to a vertical surface.

Any of the dispensers described herein can be mounted to a surface. For example, FIG. 2B is a schematic side view of the dispenser of FIG. 2A attached or mounted to a vertical surface 106. The vertical surface may be, for example part of a wall, cubicle, medication cart, nurses' office, inside an ambulance, or any other vertical surface accessible to health care professionals. Exemplary means of attachment 119 may include nuts and bolts, rivets, screws, nails, locks, latches, wires, joints, soldering, welding, gluing and the like. In any of the embodiments described herein, the housing 110 of the dispenser may include mounting brackets for coupling the dispenser to the vertical surface. In some cases, the dispenser may be mounted horizontally onto a horizontal surface.

The dispenser may include a source 151 of barrier material in the form of film 150. The source 151 may be supported within the chamber of the housing. The film 150 may extend from the source 151 such that a distal portion of the film exits the opening 120 and drapes over the recess 130.

Figure 2C:
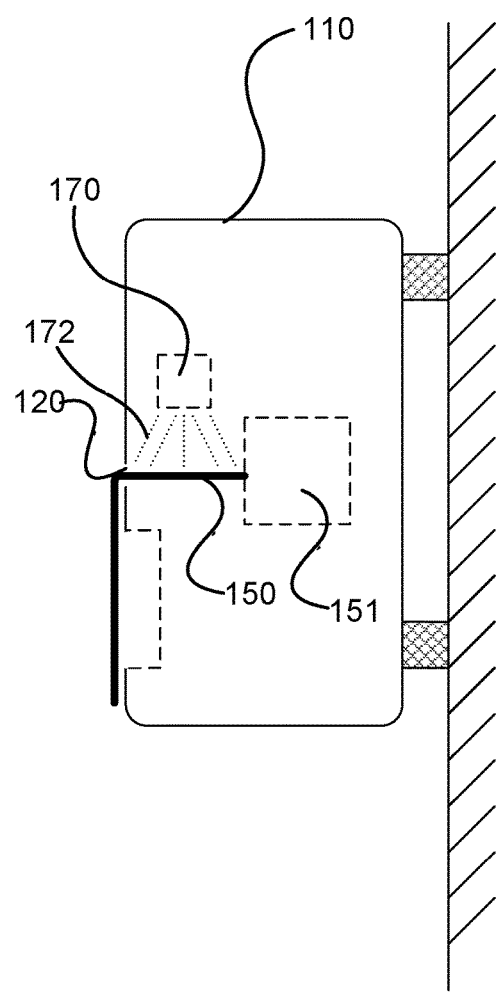
FIG. 2C is a schematic cross-sectional side view of the dispenser of FIG. 2A further comprising a UV light source, in accordance with an embodiment.

Optionally in any of the embodiments described herein, the dispenser may further include an energy source 170, for example as shown in FIG. 2C. The energy source may be provided within the chamber of the housing 110. The energy source may comprise a UV light source configured to illuminate UV/UV-C light 172 onto the film 150. The UV light source may comprise one or more UV-LEDs. The UV light source may be powered by a power supply located on the dispenser or remote to the dispenser. In any of the embodiments described herein, the UV light source can be powered by a solar panel. The solar panel may comprise one or more solar energy cells. The solar panel can be mounted on the dispenser, for example on a front, side or top portion of the housing 110. The solar panel may include monocrystalline silicon or any other semiconductor materials for harnessing solar energy. In some cases, the solar panel may be configured to output power, for example 0.2 W or higher. The solar panel can be configured to provide any power output, depending on the size of the chamber, the amount or thickness of the barrier material to be irradiated, the type of barrier material, etc. The solar panel may be formed having any shape, size and/or design to match the housing, and can be located on a portion of the housing that does not interfere with the barrier dispensing operation of the dispenser or the operation of the solar panel.

The UV light source may be configured to illuminate a top portion of the film between the source 151 and the opening 120, for example as shown in FIG. 2C. Alternatively, the UV light source may be configured to irradiate the film from a plurality of directions (e.g. top, bottom and lateral sides), thereby effectively providing a UV chamber/bath/shower for sterilizing the film prior to use, and prior to application of the film to a stethoscope head.

Figure 3A:
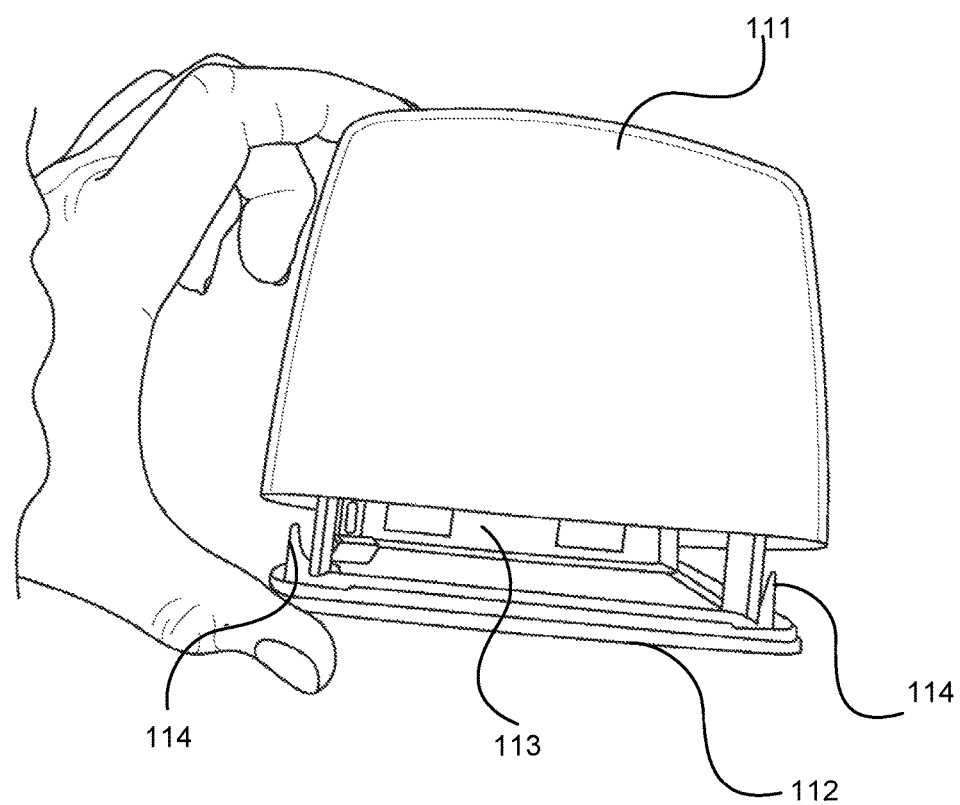
FIG. 3A is a perspective view showing a housing assembly of a barrier dispenser in accordance with an embodiment.

FIG. 3A is a perspective view showing a housing assembly of a barrier dispenser, in accordance with an embodiment which may include FIG. 1A or any of the embodiments described in this specification. The housing 110 may include a cover 111 and a base 112 configured to be coupled together. In some cases, the cover may be detachably coupled to the base such that the cover can be completely removed from the base via a locking/unlocking mechanism (e.g. snapfits, screws, etc.). In some cases, the cover may be rotatably coupled to the base using hinges. The hinges may be coupled to pivot pins such that the cover can rotate relative to the base. The cover may be closed or opened. A chamber 113 is provided within the housing when the cover is in a closed position. The cover can be opened by releasing snapfits 114 or any other type of unlocking mechanisms. The cover can be opened to allow a user to load a source of barrier material (e.g. a roll of film) into the housing. This allows an operator to easily access the inside of the dispenser, especially when replacing the film, or to allow easy cleaning of the chamber.

Figure 3B:
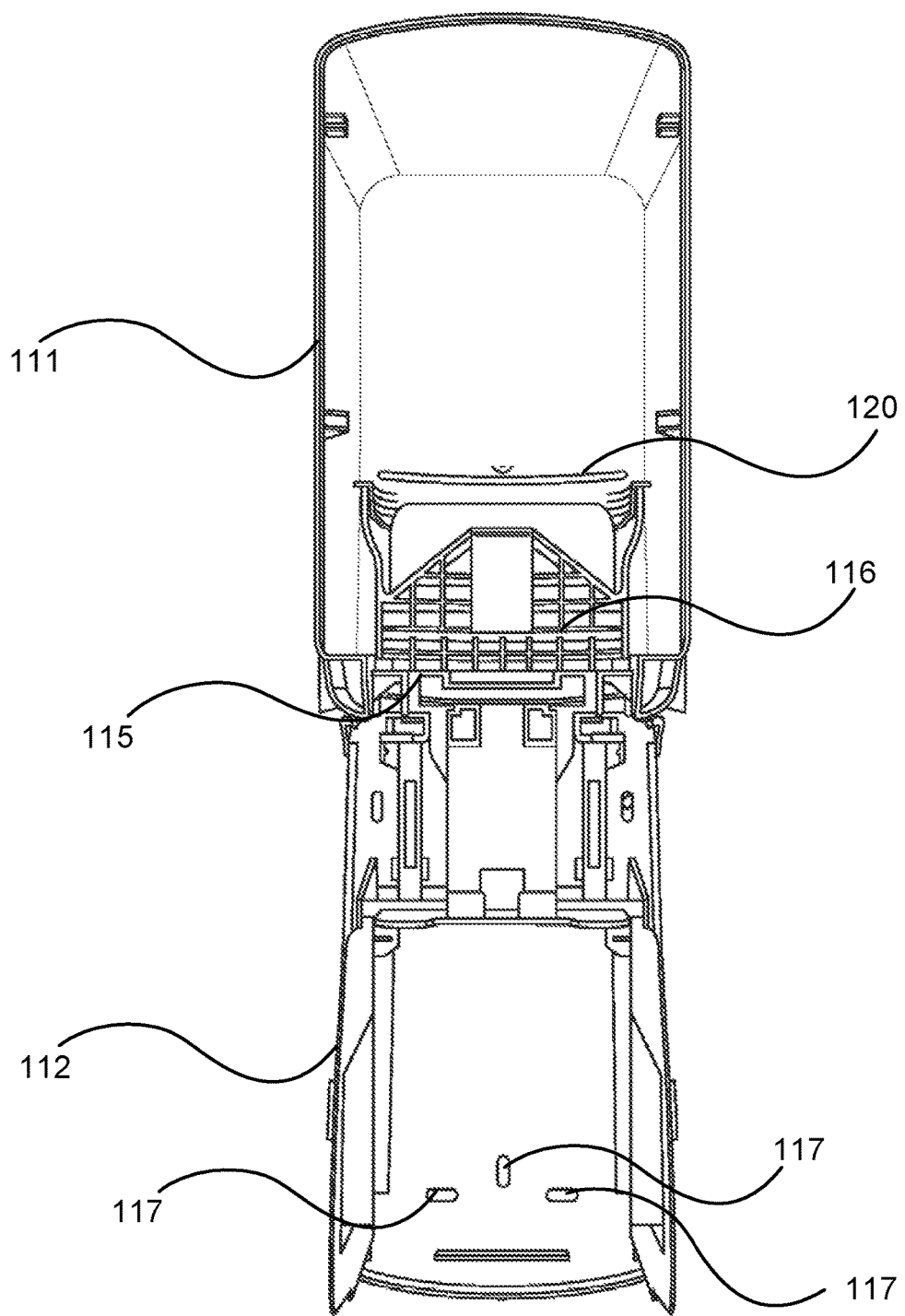
FIG. 3B is a perspective view showing an internal structure of the barrier dispenser of FIG. 3A.

FIG. 3B is a perspective view showing an internal structure of the barrier dispenser of FIG. 3A. The cover 111 can be opened, for example by rotating the cover about hinges 115, to expose the inside of the housing. The opening 120 may be formed on the cover. The recess 130 (not shown) may be provided on a front side of the cover. Optionally in any of the embodiments disclosed herein, ribs 116 may be provided to reinforce a rear portion of the recess. Structural reinforcement can be advantageous for prolonging the life of the dispenser since the recess is subject to repeated forces by a user during application of the barriers to the stethoscope head for multiple users (patient encounters). The base 112 may include a plurality of mounting holes 117-1, 117-2, and 117-3 for allowing the dispenser to be attached a structure (e.g. a wall). Optionally in any of the embodiments disclosed herein, an energy source (e.g. a UV/UV-C light source) may be provided on the inside of the housing, for example as described later in the specification and illustrated in FIG. 4E.

Figure 4A:
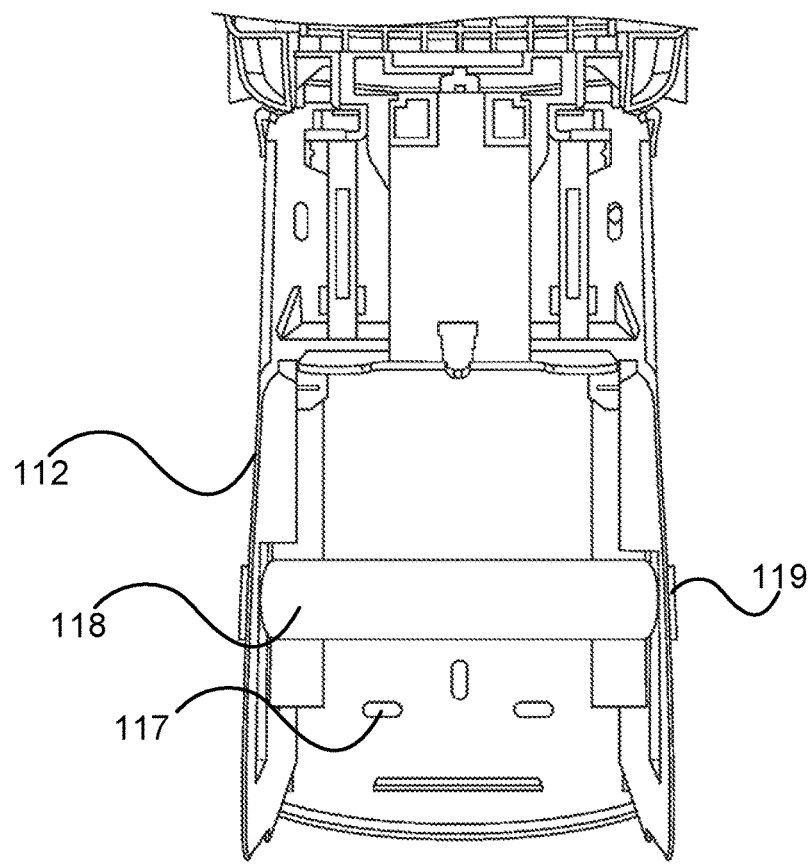
FIG. 4A is a perspective view showing a roller coupled to an inner portion of a barrier dispenser, in accordance with an embodiment.
Figure 4B:
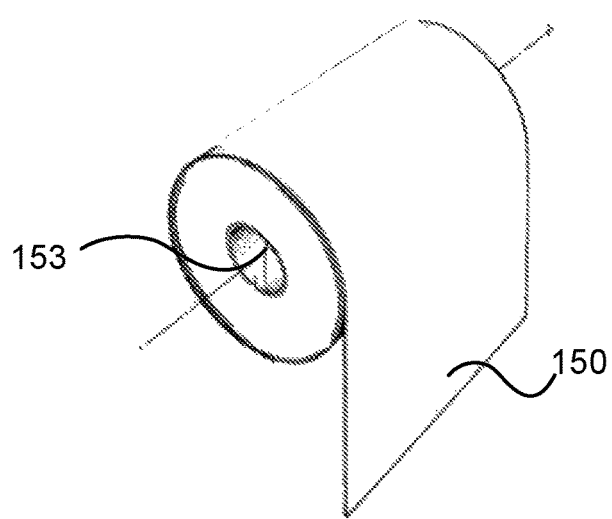
FIG. 4B is a perspective view showing a roll of film that is configured to be coupled to the roller of FIG. 4A.
Figure 4C:
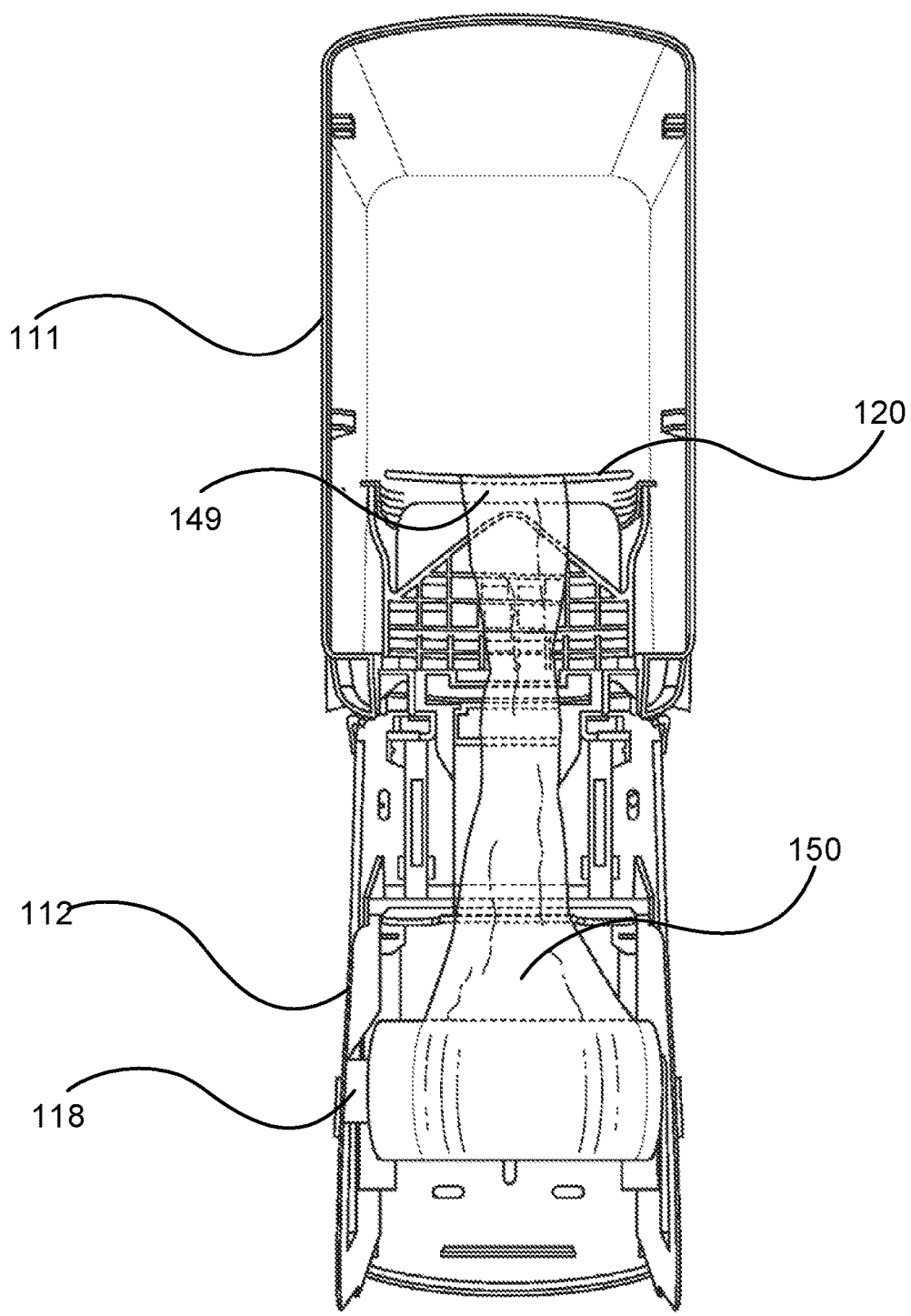
FIG. 4C is a perspective view showing the roll of film coupled to the roller and extending to a slot opening of the barrier dispenser, in accordance with an embodiment.

FIG. 4A is a perspective view showing a roller coupled to an inner portion of the barrier dispenser which may be in any of the embodiments disclosed herein. A roller 118 may be coupled to the base 112. The roller may be rotatably coupled to the base via hinges or tabs 119. The roller may be configured to support and dispense a source of barrier material (e.g., a roll of film 150 as shown in FIG. 4B). The film may be wound around a longitudinal tube 153 multiple times to form the roll of film. The roller may be detached from the housing, inserted through the tube (roll of film), and then mounted back into the housing, for example as shown in FIG. 4C. The base may include a dispense mechanism (not shown) operably coupled to the roller and configured to cause the roller to rotate. The dispense mechanism may include, for example a knob, crank, automated mechanism, bar, stored energy mechanism, etc. When a roll of film is mounted to the roller, rotation of the roller in one direction (clockwise or counterclockwise) can cause the roll of film to unroll and dispense. A user can manually dispense the film, for example by cranking the bar or turning the knob on the housing, or pulling up a sheet in a manually dispensed scenario. In some cases, the dispense mechanism may be omitted for manually dispensed barriers. For example, the dispenser may be configured to automatically dispense a predetermined amount of film to form a single barrier for each use or patient encounter. Optionally in any of the embodiments disclosed herein, the dispense mechanism may include a sensor that detects when a scope is adjacent the housing and automatically triggers the dispense mechanism to dispense the film.

FIG. 4C is a perspective view showing a source of film coupled to the roller and extending to an opening of the barrier dispenser that may apply to any embodiment disclosed herein. A source of the barrier material may include a roll of film 150. The roll of film may be mounted onto the roller 118. The roll of film can be unrolled such that a distal portion 149 of the film extends to the opening 120. The distal portion of the film can be inserted through the opening to extend beyond the cover 111. The distal portion of the film can be extended such that it hangs in proximity to the recess of the housing, as described elsewhere herein.

Figure 4D:
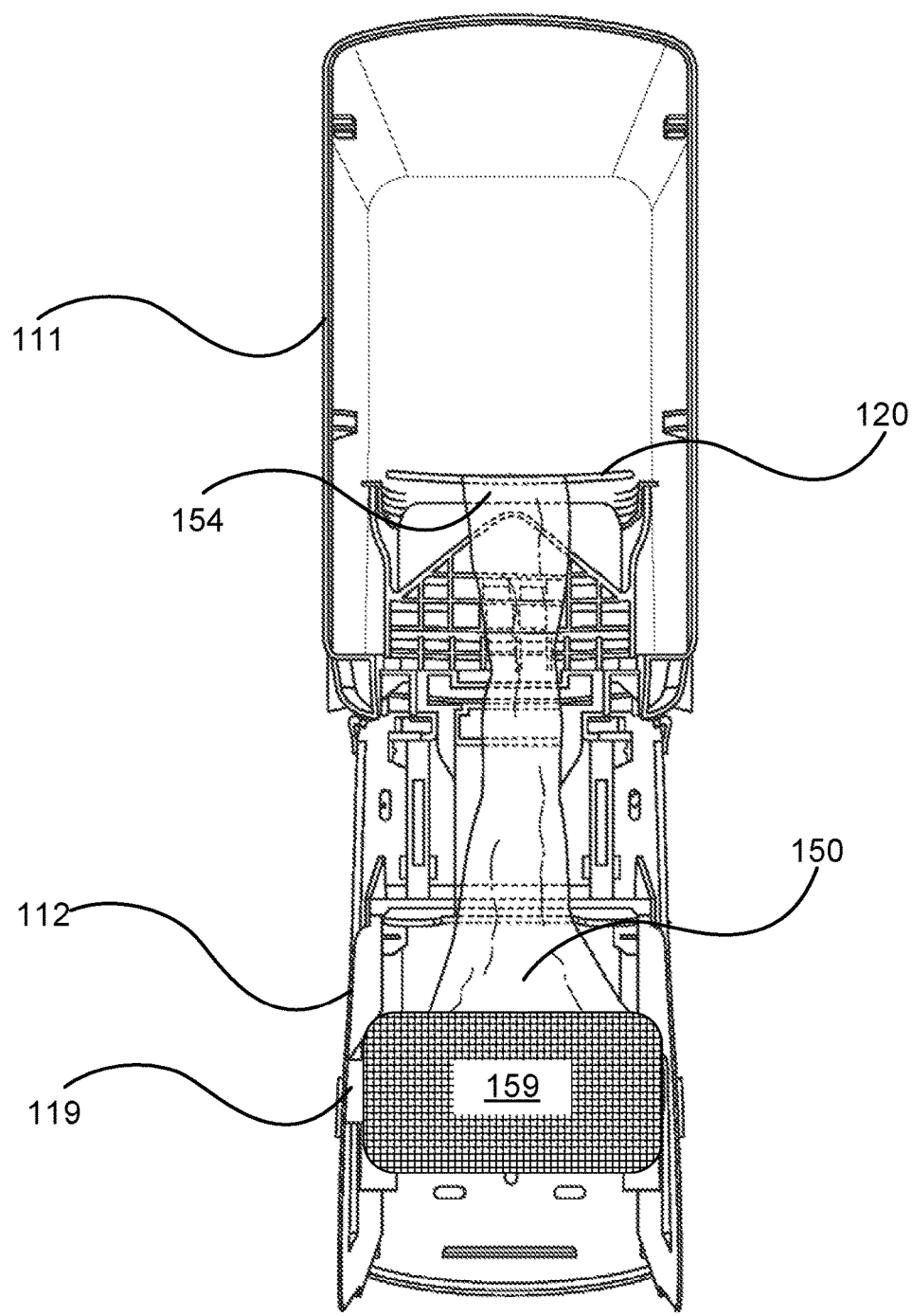
FIG. 4D is a perspective view showing the roll of film being provided in a cassette, in accordance with an embodiment.

FIG. 4D is a perspective view showing the roll of film being provided within a cassette 159 that may apply to any embodiment disclosed herein. The cassette can help to keep the roll of film in a clean environment, and protect the film from contaminants, dust, microbes, germs, bacteria, moisture, etc. The cassette can be easily coupled to the base via hinges or tabs 119 to permit quick loading/unloading of the cassette. The cassette may comprise a stored energy mechanism for automatic film dispensing. For example, the stored energy mechanism may include a spring that is energized when a user pulls and withdraws film from the dispenser. The spring can be configured to move the roll of film to dispense more film (or a preset amount of film) upon release of the stored energy in the spring. The cassette can be removed from the housing when the film has been depleted, to be replaced by another new cassette.

Figure 4E:
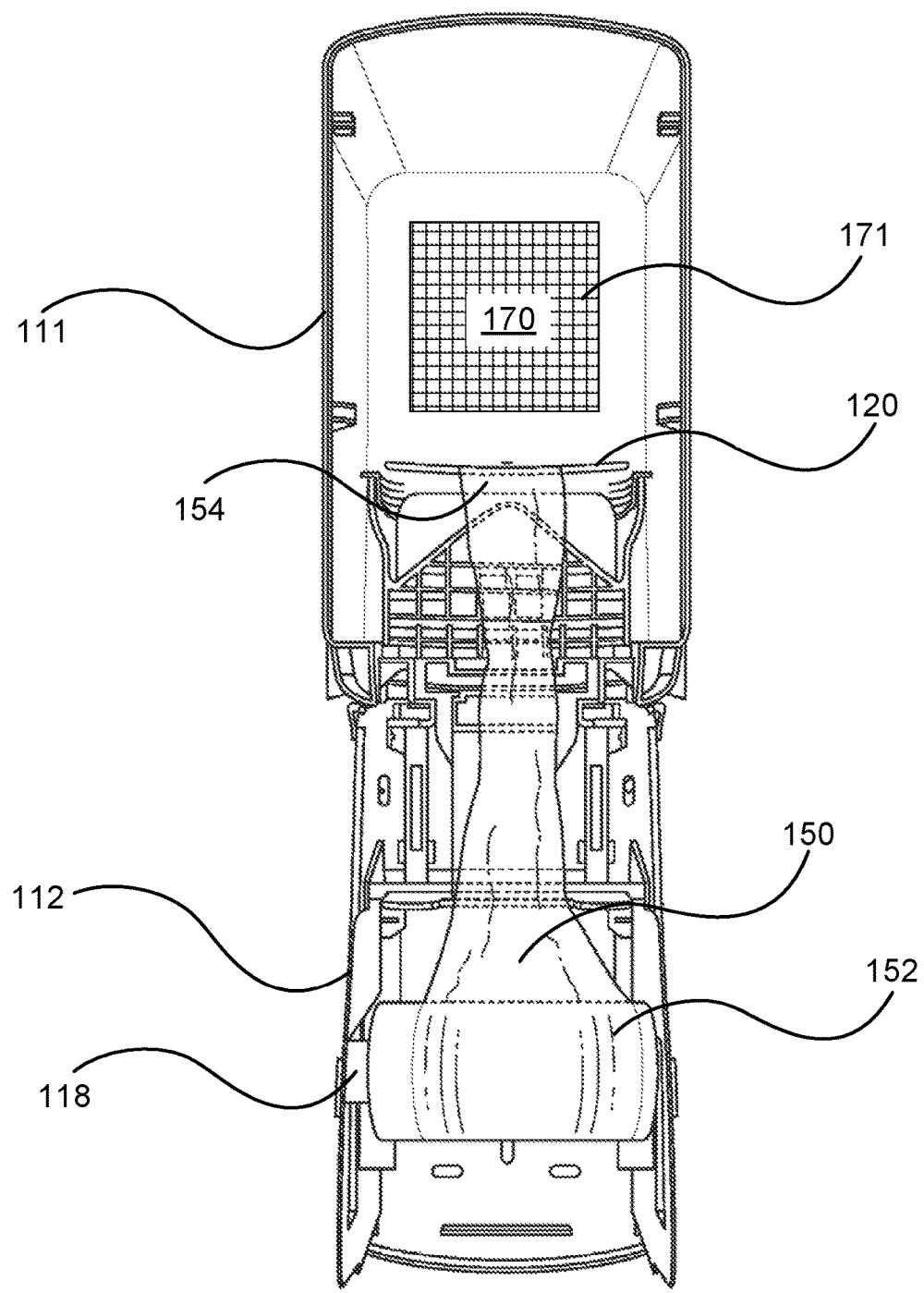
FIG. 4E is a perspective view showing a UV light source disposed within the housing, in accordance with an embodiment.

FIG. 4E is a perspective view showing a UV light source disposed within the housing, that may apply to any embodiment disclosed herein. As previously described, the dispenser may optionally include an energy source 170. The energy source may comprise a UV light source configured to illuminate UV/UV-C light 172 onto the film 150. The UV light source may be provided within the chamber of the housing 110. For example, as shown in FIG. 4E, the UV light source may be attached to or integrally formed on an inside of the cover 111. The UV light source may comprise one or more UV-LEDs. For example, a plurality of UV-LEDs 171 may be provided in a grid pattern on the inside of the cover. Alternatively, the UV-LEDs may be provided in a radial pattern, or any regular or irregular pattern. The plurality of UV-LEDs may be controlled, either individually or collectively, to illuminate the film inside the housing with UV/UV-C. The UV light source may be configured to illuminate a portion or all of the film stored within the housing. Alternatively, the UV light source may be configured to irradiate the film from a plurality of directions (e.g. top, bottom and lateral sides from within the chamber), thereby effectively providing a UV chamber/bath/shower for sterilizing the film prior to use, and prior to application of the film to a stethoscope head.

The UV light source shown in FIG. 4E or any of the embodiments disclosed herein may be powered by a power supply located on the dispenser or remote to the dispenser. For example, in any of the embodiments described herein, the UV light source can be powered by a solar panel. The solar panel may comprise one or more solar energy cells. The solar panel can be mounted on the dispenser, for example on an exterior front, side or top portion of the housing 110. In FIG. 4E, the solar panel may be mounted (not shown) on an outer surface of the cover 111 that is opposite to a surface on which the energy source 170 (UV light source) is mounted. The solar panel and the energy source 170 (UV light source) are electrically coupled together such that the solar panel is configured to provide power to the UV light source (e.g. UV-LEDs). The solar panel may include monocrystalline silicon or any other semiconductor materials for harnessing solar energy. In some cases, the solar panel may be configured to output power, for example 0.2 W or higher. The solar panel may be formed having any shape, size and/or design to match the housing, and can be located on a portion of the housing that does not interfere with the barrier dispensing operation of the dispenser or the operation of the solar panel.

Figure 5A:
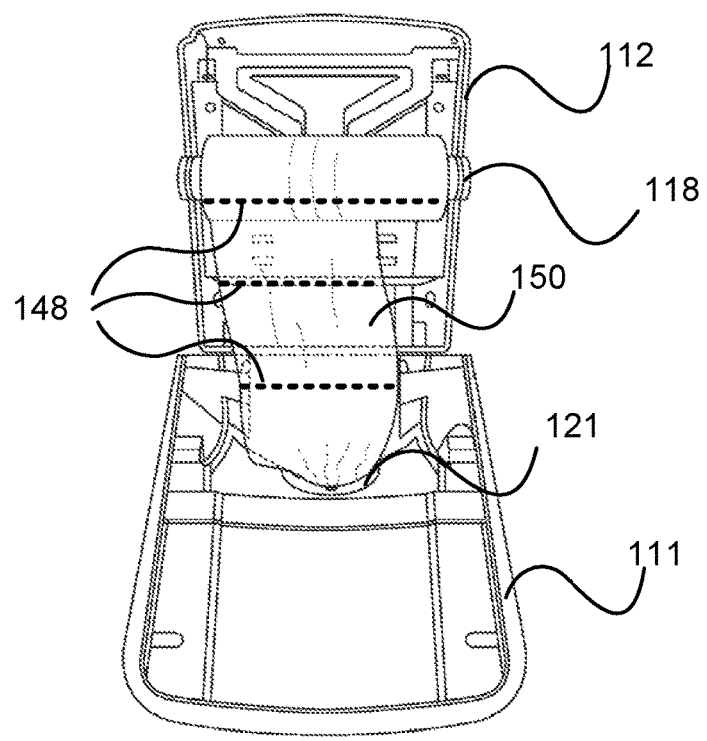
FIG. 5A is a perspective view showing a roll of film coupled to a roller and extending to a circular opening of a barrier dispenser, in accordance with an embodiment.
Figure 5B:
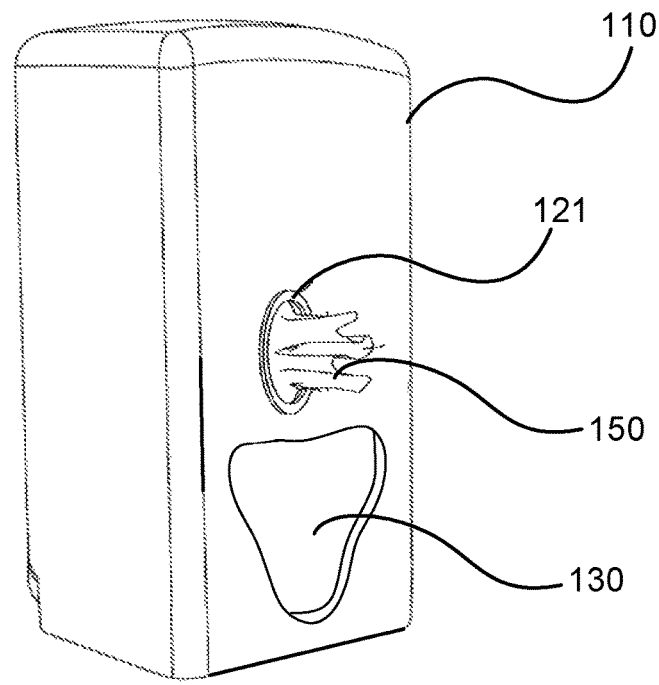
FIG. 5B is a perspective view of the assembled dispenser of FIG. 5A and shows film being dispensed from the circular opening, in accordance with an embodiment.

FIG. 5A is a perspective view showing a roll of film coupled to a roller and extending to a circular opening of a barrier dispenser, that may apply to any embodiment disclosed herein. FIG. 5B is a perspective view of the assembled dispenser of FIG. 5A and shows the film being dispensed from the circular opening. The dispenser may include a substantially circular opening 121 instead of the horizontal slot opening 120 described elsewhere herein. The opening 121 may also be formed having an elliptical shape or any shape that permits the roll of film 150 to be dispensed from the opening without impeding movement of the film. The roll of film may comprise perforations 148 that allow sheets of film to be easily and manually separated by the user by hand. FIG. 5B shows a sheet of film 150 partially extending from the circular opening 121. A user can pull out the film, and separate the sheet from the remaining roll of film by tearing along the perforations. Accordingly, the dispenser shown in FIGS. 5A and 5B optionally need not include any separating mechanism for cutting the film, since the film can be easily separated by hand along the perforations.

Figure 6A:
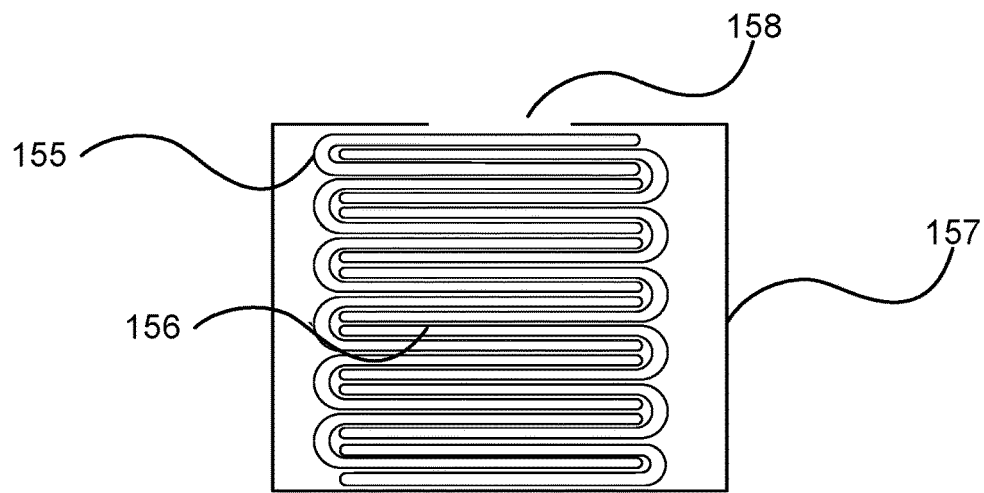
FIG. 6A is a schematic view of a source of barrier material provided in the form of interleaved stacked sheets, in accordance with an embodiment.
Figure 6B:
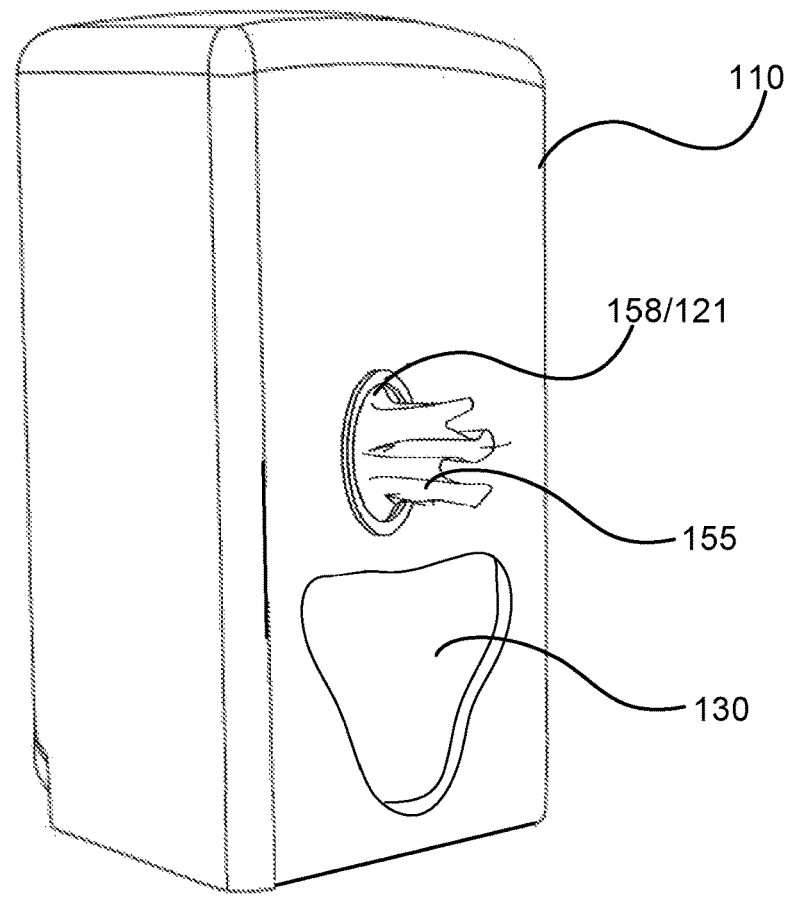
FIG. 6B is a perspective view of a barrier dispenser showing the dispense of a single sheet from the interleaved stacked sheets of FIG. 6A, in accordance with an embodiment.

FIG. 6A is a schematic side view of barrier material provided in the form of interleaved stacked sheets, that may apply to any embodiment disclosed herein. FIG. 6B is a perspective view of a barrier dispenser showing the dispense of a single sheet from the interleaved stacked sheets of FIG. 6A. Referring to FIG. 6A, the barrier material may be provided as a plurality of separate sheets 155 that are folded, interleaved 156 and stacked together in the configuration as shown. The stack of interleaved sheets may be stored in a sheet container 157. The sheet container comprises an opening 158 that is configured to permit a sheet that is closest to the opening to be removed. The sheets are interleaved such that when a user pulls out and removes a sheet from the opening 158, an underlying sheet beneath would be transformed from a planar folded configuration to a three-dimensional configuration. The underlying sheet would then extend out from the opening to replace the sheet that was removed, thereby allowing a user to retrieve sheets from the container easily without having to probe into the container with fingers. FIG. 6B shows the three-dimensional configuration of a single sheet extending out of the opening 158 of the container and the opening 121 of the housing. In the example of FIGS. 6A and 6B, the dispenser may include a substantially circular opening 121 instead of the horizontal slot opening 120 described elsewhere herein. The opening 121 may also be formed having an elliptical shape or any shape that permits the interleaved stacked sheets to be dispensed from the opening. For example, the shape and/or size of the opening may be configured based on the interleaving pattern of the sheets, so as to allow separate sheets to be dispensed easily while preventing the underlying sheet from falling back into the sheet container.

Figure 7:
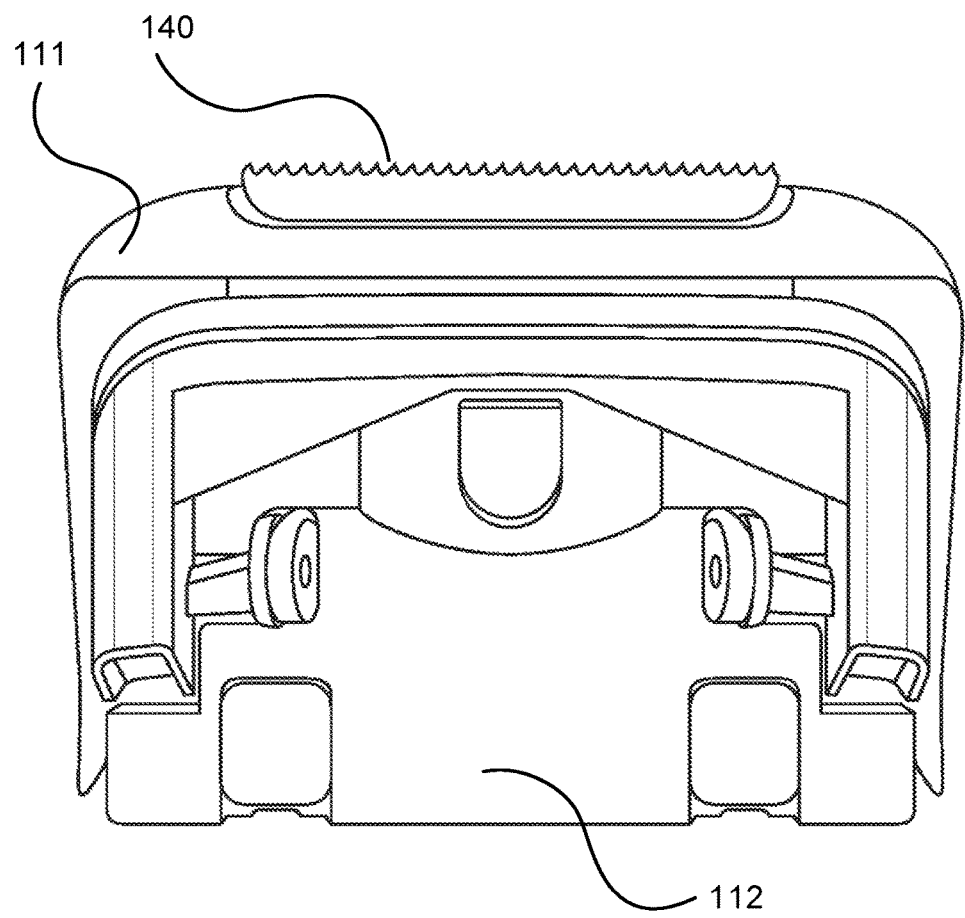
FIG. 7 is a bottom perspective view showing a cutting edge of a barrier dispenser in accordance with an embodiment.

FIG. 7 is a bottom perspective view showing a cutting edge of a barrier dispenser that may apply to any embodiment disclosed herein. As previously described, the dispenser may optionally include a cutting edge 140 and optionally may be used with any dispenser disclosed herein. The cutting edge may be located on a bottom front portion of the cover 111. The cutting edge may be detachably coupled to the cover, or integrally formed as part of the cover. The cutting edge can be fixed or movable. For example, a sliding cutter may also be used. Optionally in any of the embodiments disclosed herein, the cutting edge may be located on the base 112 instead of the cover. The cutting edge can include a serrated sharp edge that is used to cut and release a portion of the film after the barrier has been applied to a stethoscope head, or it may be a straight cutting edge. The cutting edge can be configured to cut and release a portion of the film after the film has been applied to a stethoscope head to form a barrier. The length of the cutting edge can be customized to permit an entire width of the film to be cut. In some cases, a longitudinal length of the cutting edge may be the same or longer than the width of the film to be cut. The cutting edge may be oriented at an angle that permits the film to be cut easily when a user pulls down the film and applies pressure to the film over the cutting edge. In any of the embodiments described herein, the cutting edge or a cutter can be omitted, if the barrier material is provided in the form of perforated film, or as a stack of separate interleaved sheets that can be manually dispensed without requiring cutting.

FIGS. 8A through 8F illustrate an exemplary method of moving a stethoscope head within a recess to apply a barrier to the stethoscope head, in accordance with any of the embodiments disclosed herein. FIGS. 9 through 17 are perspective views showing application of the barrier to the stethoscope head in accordance with the method shown in FIGS. 8A-8F as will be described below. The stethoscope head can be translated and/or rotated within the recess. A user can move the stethoscope head in a clockwise or counterclockwise direction within the recess, and by any amount (for example, ranging from about 10 degrees to 360 degrees). The translation and/rotation can cause the film to wrap around the stethoscope head, thereby forming the barrier on the stethoscope head, as described below.

Figure 9:
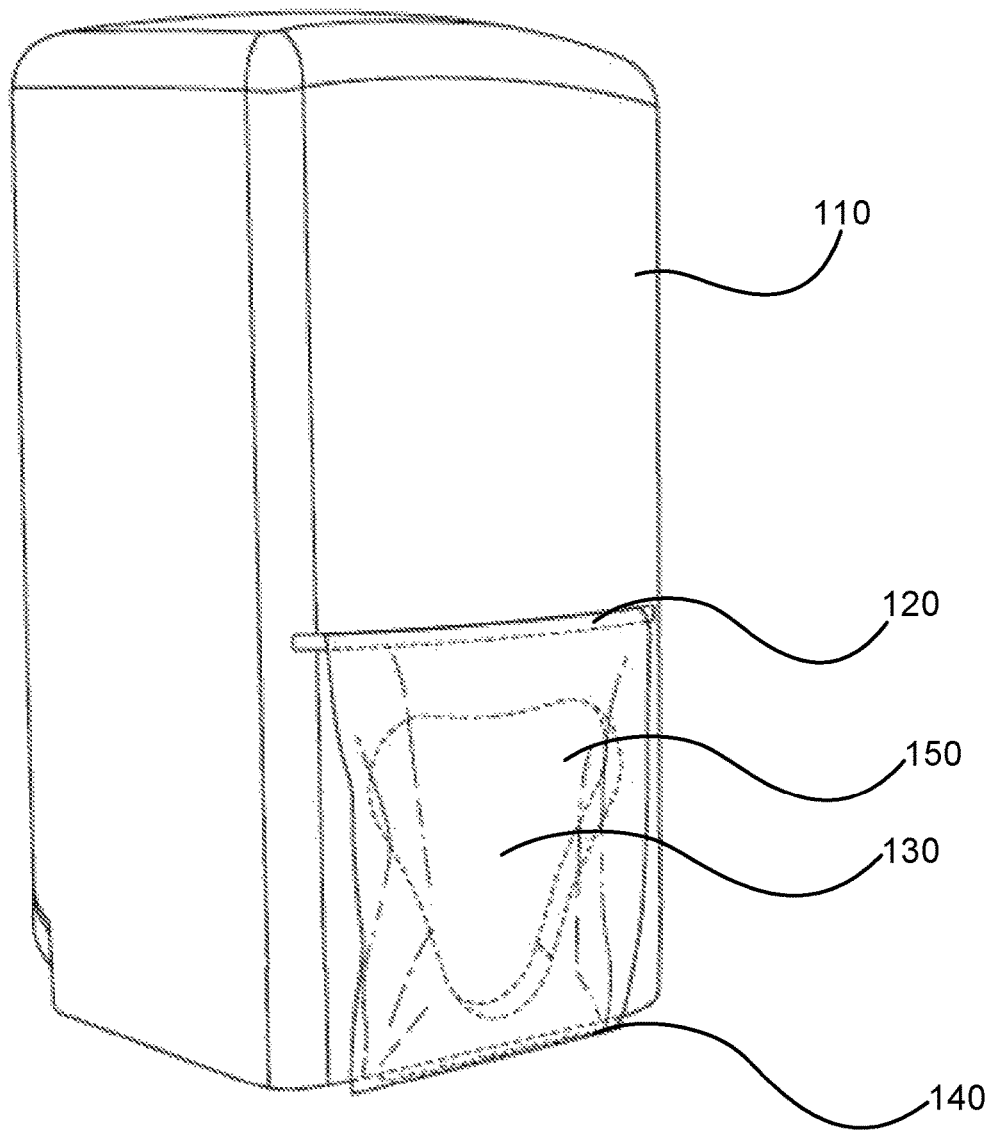

Referring to FIG. 9, the film 150 may be dispensed from the opening 120 such that it hangs over the recess 130. The extended portion of the film may completely cover the recess. In some other cases, the extended portion of the film may cover the recess partially as described elsewhere herein.

Figure 10:
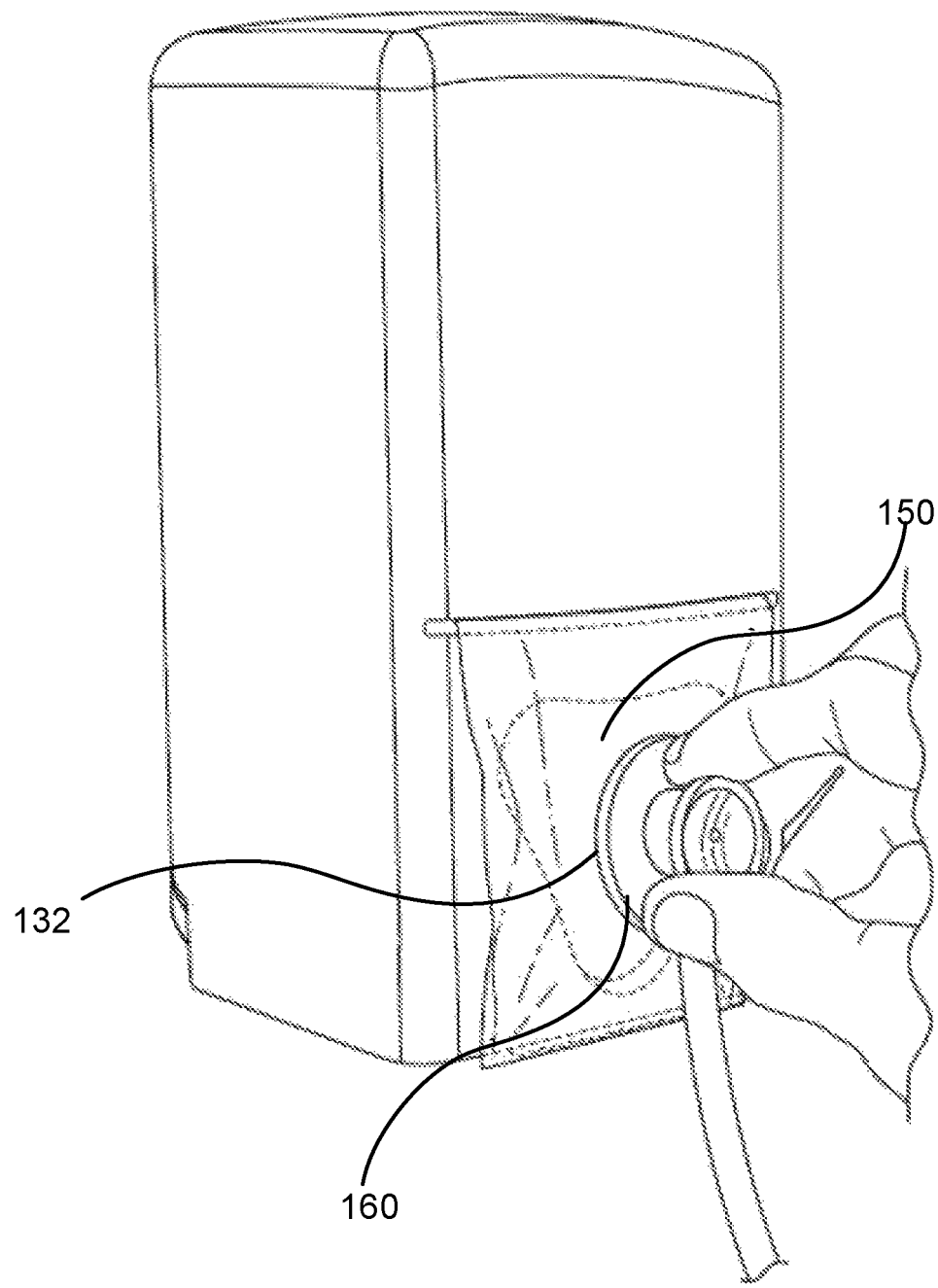

As shown in FIG. 10, a user may place a stethoscope head 160 onto the portion of the film 150 in front of the recess 130. The stethoscope head may be placed, for example substantially at or near a center 132-0 of the recess shown in FIG. 8A. Next, the user may push the stethoscope head with the film into the recess, with the film located in-between the stethoscope head and the recess. The film may be applied onto a distal surface of the stethoscope head when the user pushes the stethoscope head against the bottom surface of the recess. The film may easily attach to the stethoscope head such that light compression of the film causes the film to stick to the stethoscope head. The user may dispose of any hanging material before using, and pull an unexposed barrier before use.

Figure 8A:
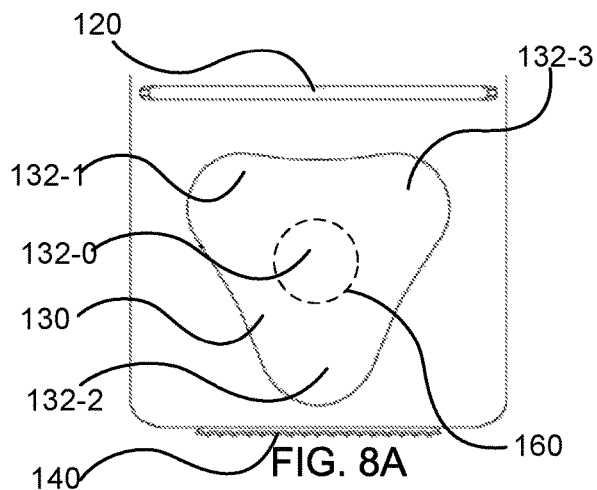
FIGS. 8A through 8F illustrate an exemplary method of moving a stethoscope head within a recess to apply a barrier to the stethoscope head, in accordance with an embodiment.
Figure 8B:
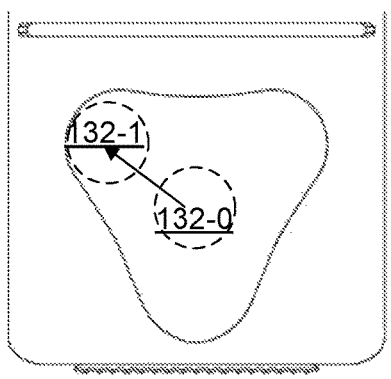
Figure 11:
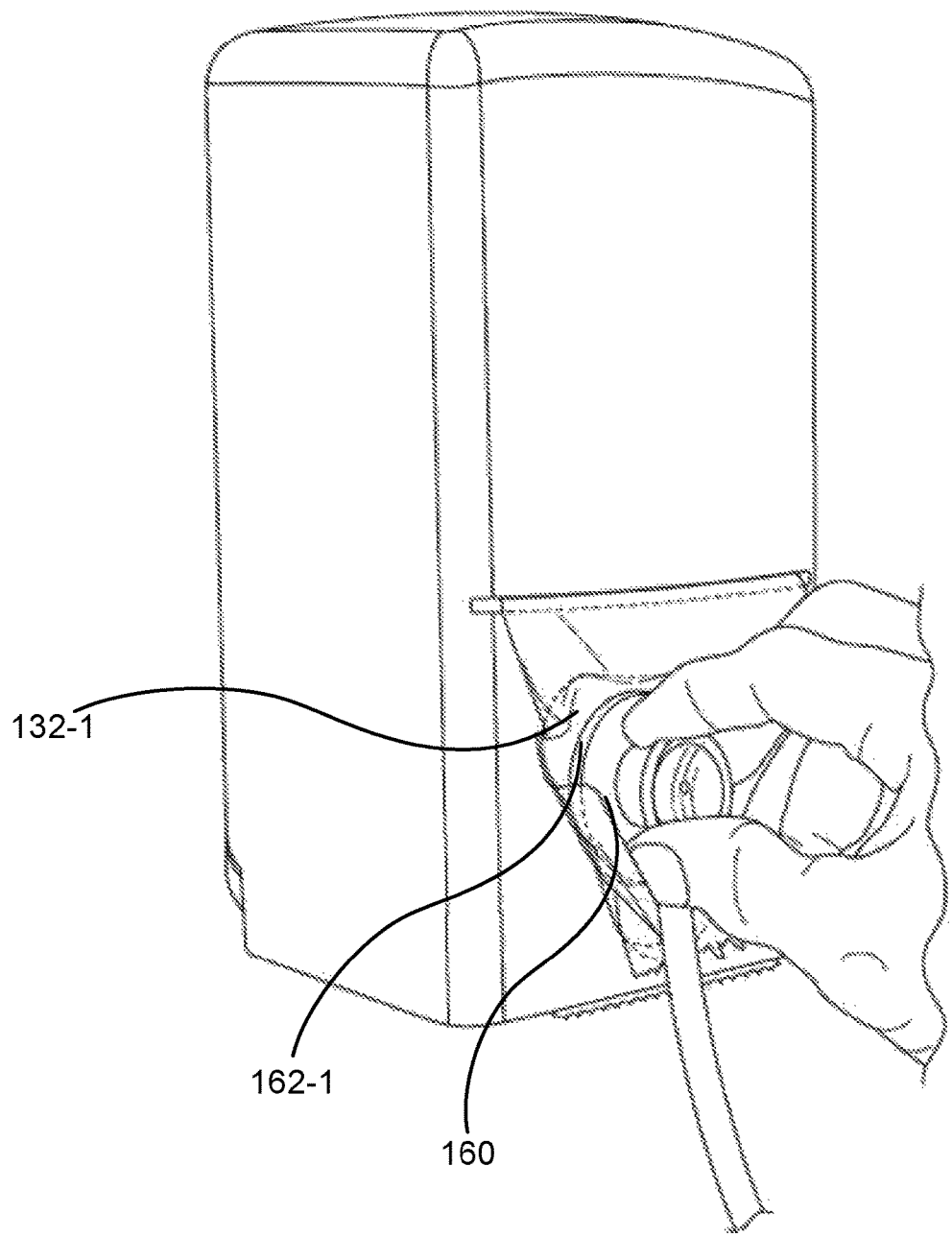

After the stethoscope head has been placed into the recess, the user may move the stethoscope head around, for example by translating and/or rotating the stethoscope head within the recess. The user may move the stethoscope head with the film inside the recess in a clockwise or counterclockwise manner. Referring to FIGS. 11 and 8B, the user may slide the stethoscope head with the film from the center 132-0 to the first lobe 132-1 located at the top left corner of the recess. When the user pushes the stethoscope head against the first lobe, a first portion of the film is pressed onto a first edge portion 162-1 of the stethoscope head. The radius of the first lobe may be configured to increase the contact area between the film and the first edge portion of the stethoscope head.

Figure 8C:
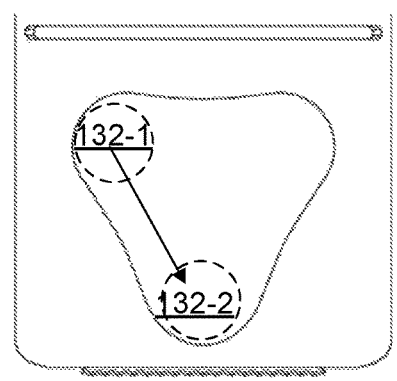
Figure 12:
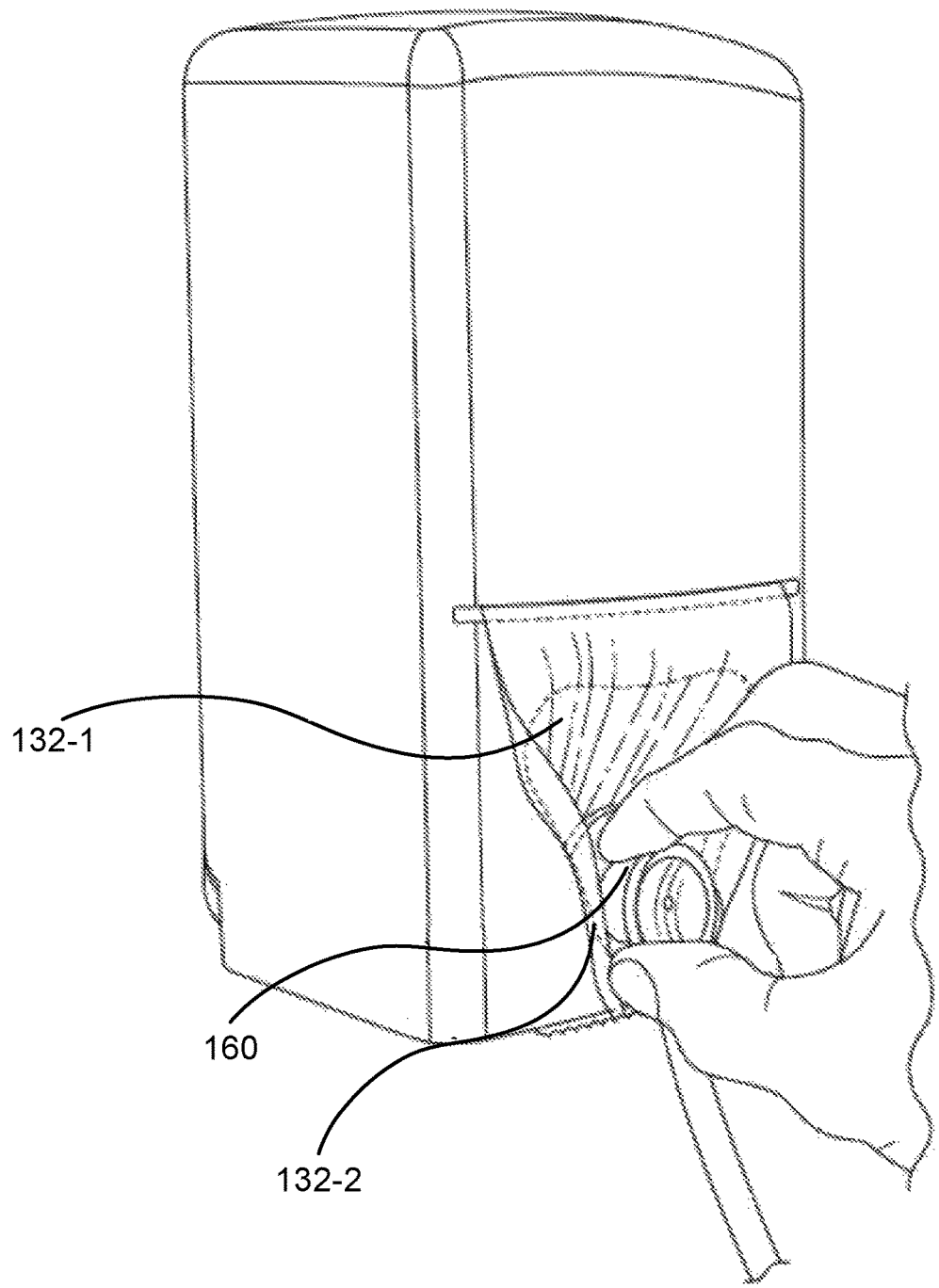

Next, referring to FIGS. 12 and 8C, the user may slide the stethoscope head with the film from the first lobe 132-1 to the second lobe 132-2 located at the bottom corner of the recess. When the user pushes the stethoscope head against the second lobe, a second portion of the film is pressed onto a second edge portion (not shown) of the stethoscope head. The second edge portion is located radially on a different portion of the stethoscope head. The radius of the second lobe may be configured to increase the contact area between the film and the second edge portion of the stethoscope head.

Figure 8D:
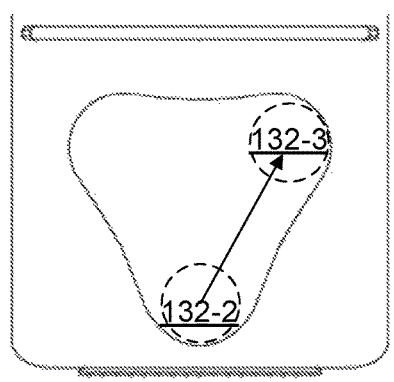
Figure 13:
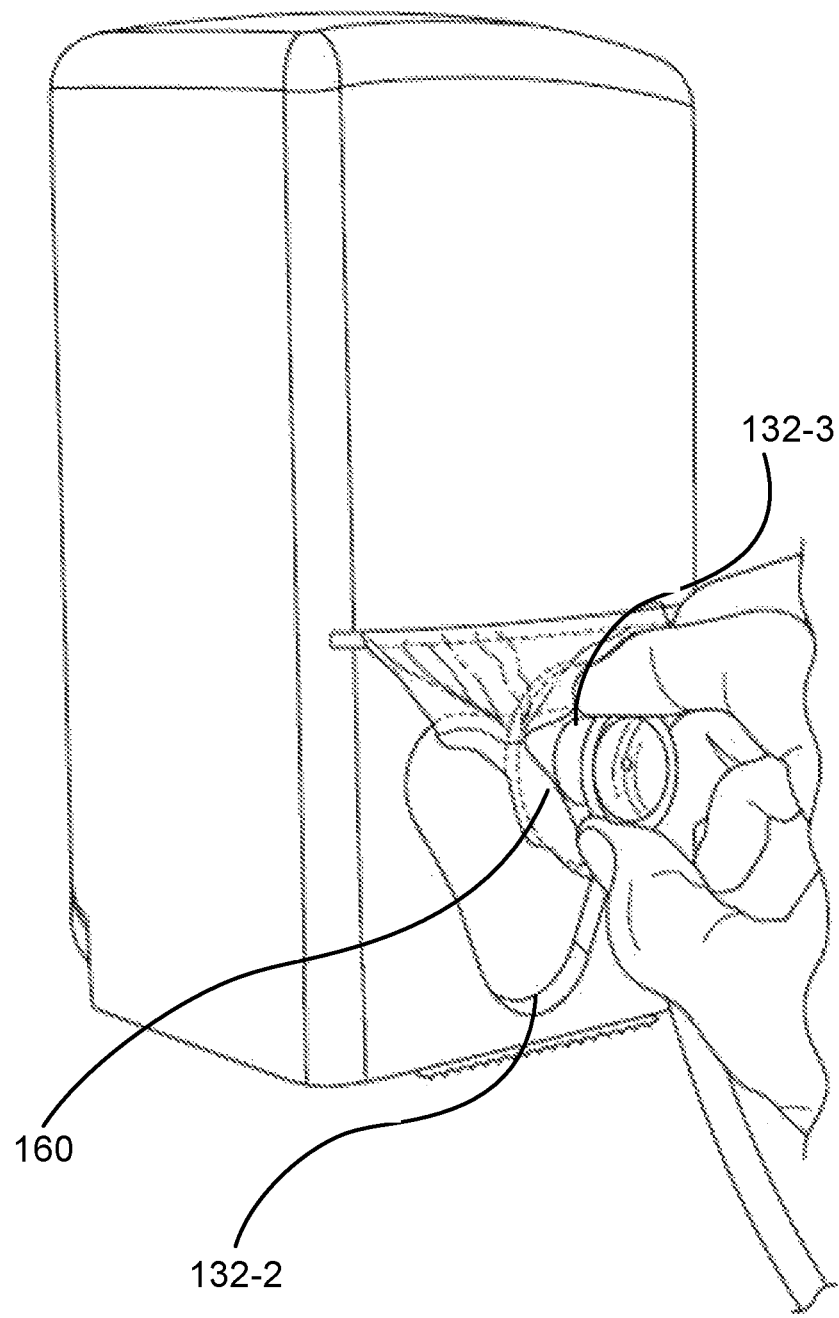

Next, referring to FIGS. 13 and 8D, the user may slide the stethoscope head with the film from the second lobe 132-2 to the third lobe 132-3 located at the top right corner of the recess. When the user pushes the stethoscope head against the third lobe, a third portion of the film is pressed onto a third edge portion (not shown) of the stethoscope head. The radius of the third lobe may be configured to increase the contact area between the film and the third edge portion of the stethoscope head. As shown in FIG. 13, the film is lifted up and moves with the stethoscope head when the stethoscope head is moved from the second lobe to the third lobe, and a portion of the recess may be exposed.

Figure 8E:
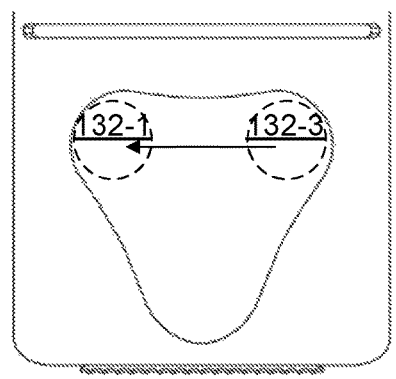
Figure 8F:
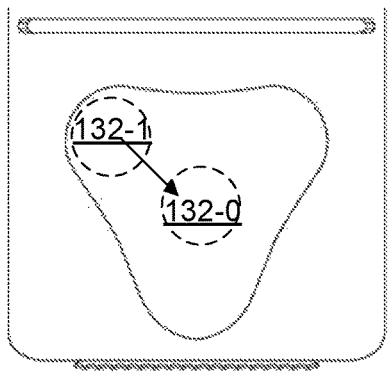
Figure 14:
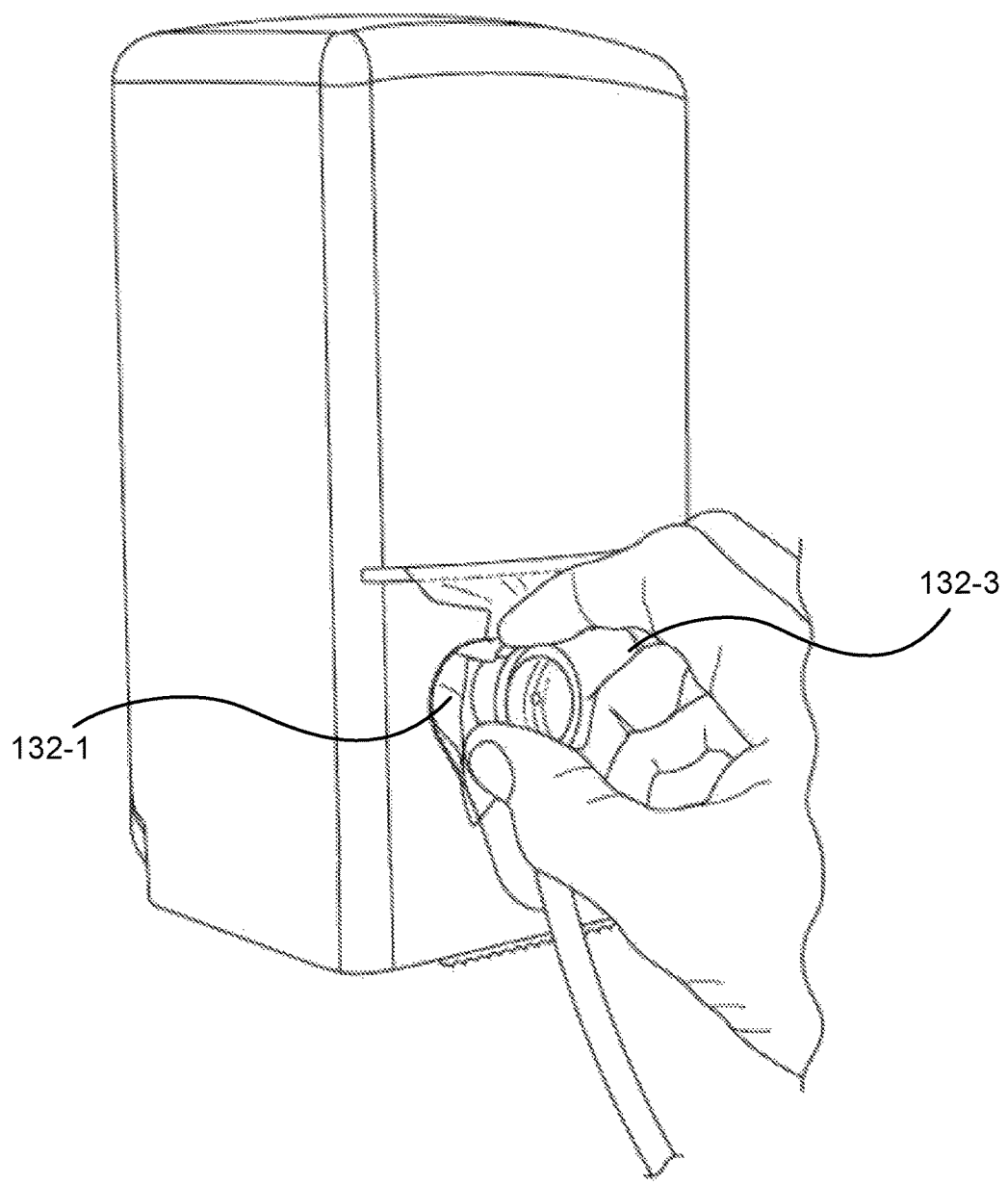

Next, referring to FIGS. 14 and 8E, the user may slide the stethoscope head with the film from the third lobe 132-3 back to the first lobe 132-1 located at the top left corner of the recess. Accordingly, the stethoscope head has moved (translated and/or rotated) in 360-degree counterclockwise within the recess between the lobes. This movement of the stethoscope head between the different lobes causes the film to wrap around different edge portions of the stethoscope head, thereby securing the film to the stethoscope head to form a barrier 152. An operator may slide the stethoscope along all or any portion of the 360 degree path described herein.

Figure 15:
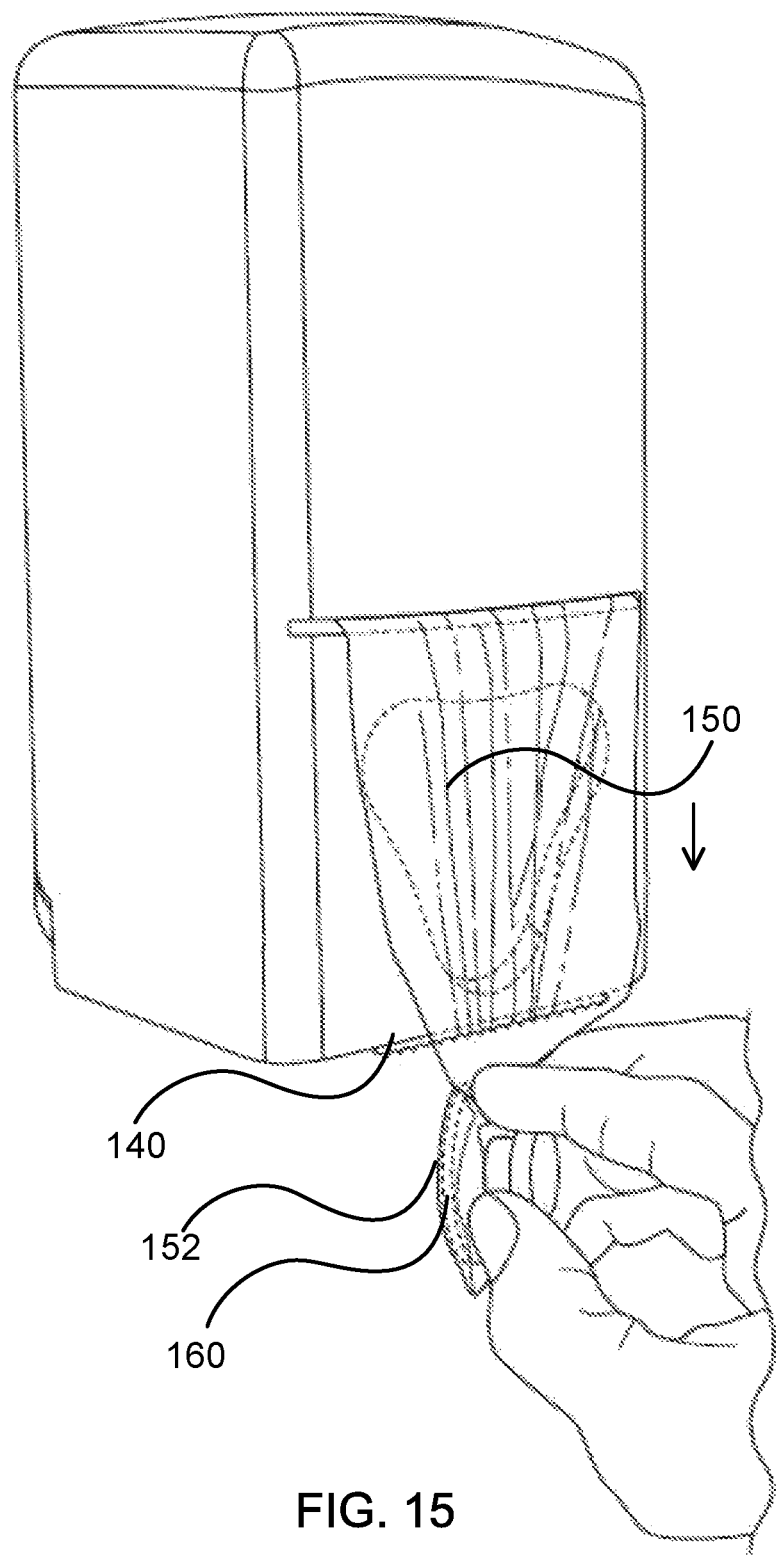
Figure 16A:
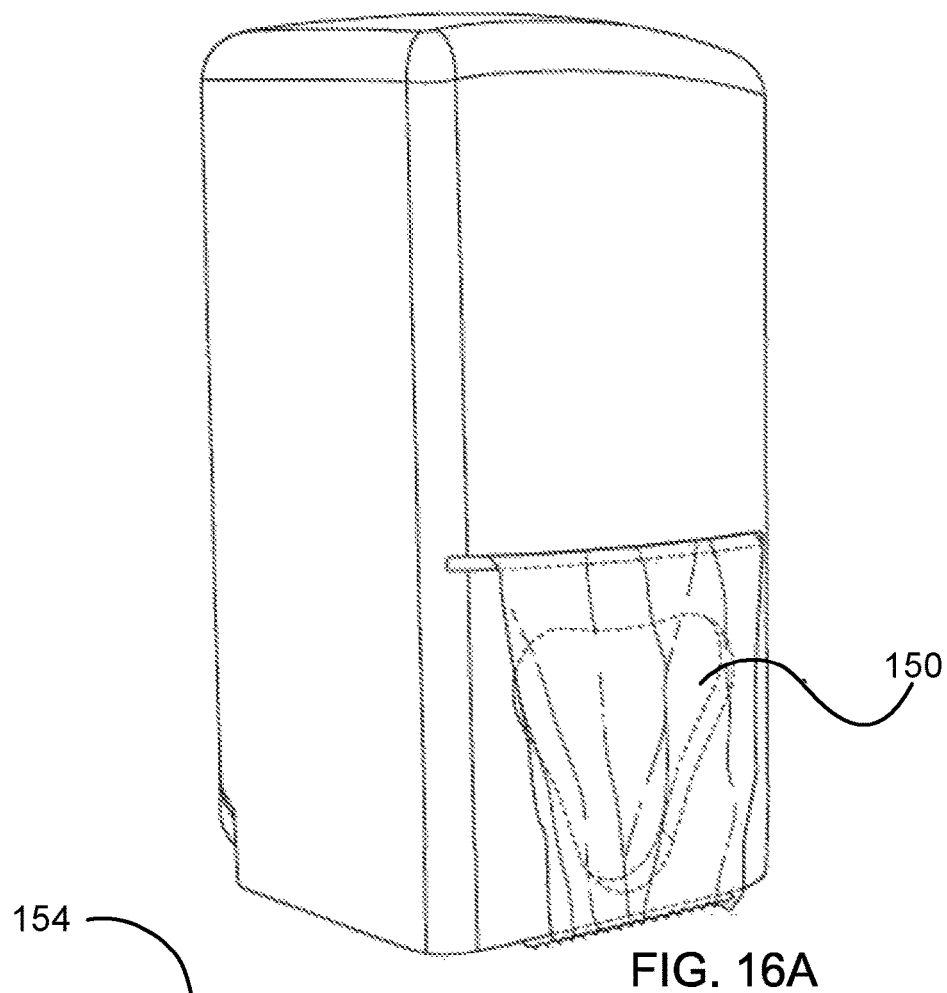
FIG. 16A is a perspective view showing the film after on the dispenser after the stethoscope head and the barrier have been released.
Figure 16B:
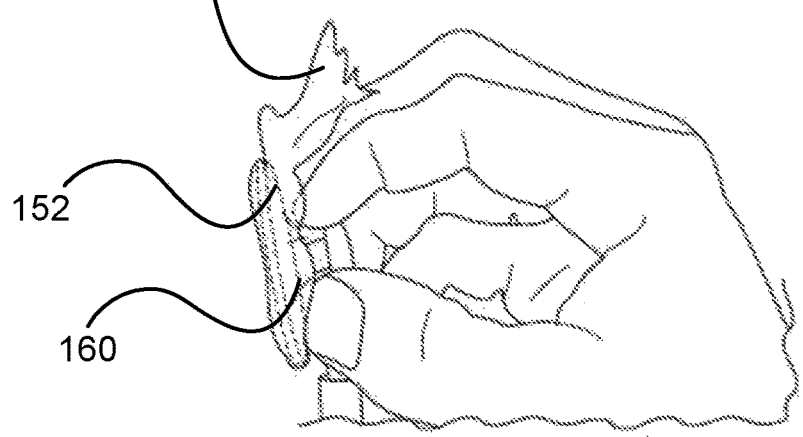
FIG. 16B is a perspective view showing the barrier being applied to the stethoscope head.
Figure 17:
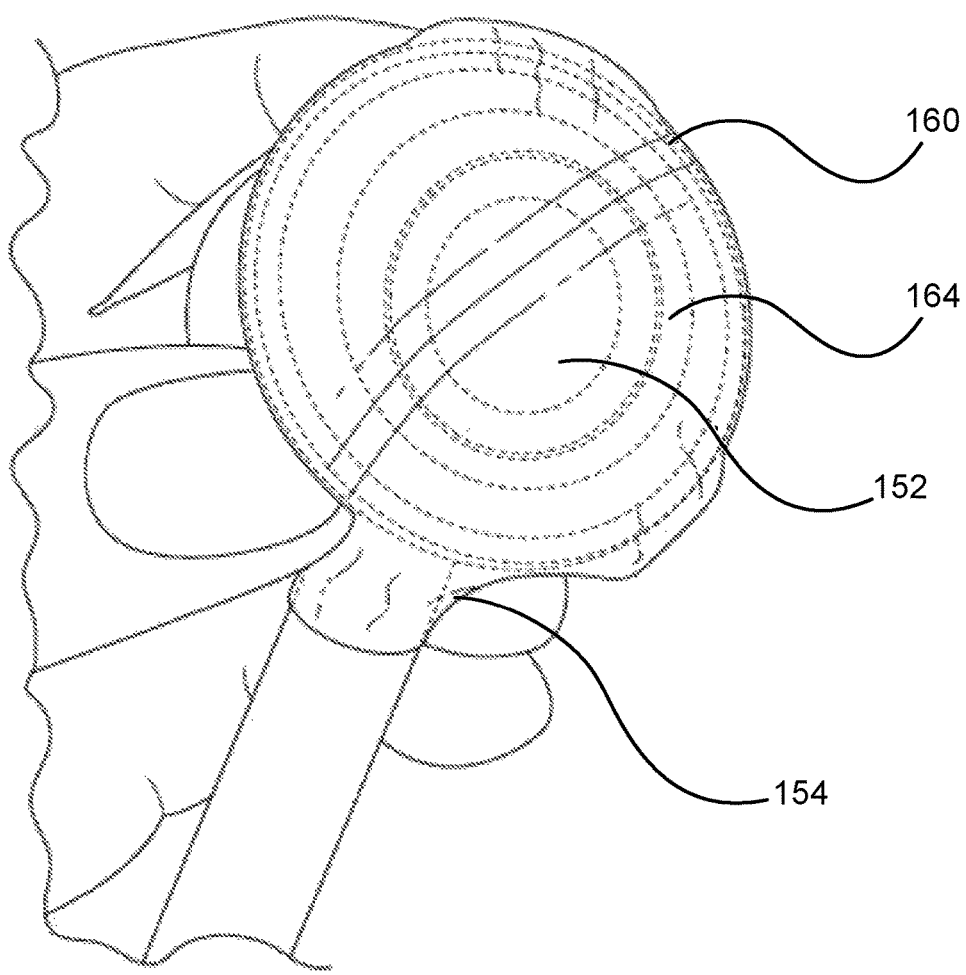
Figure 18:
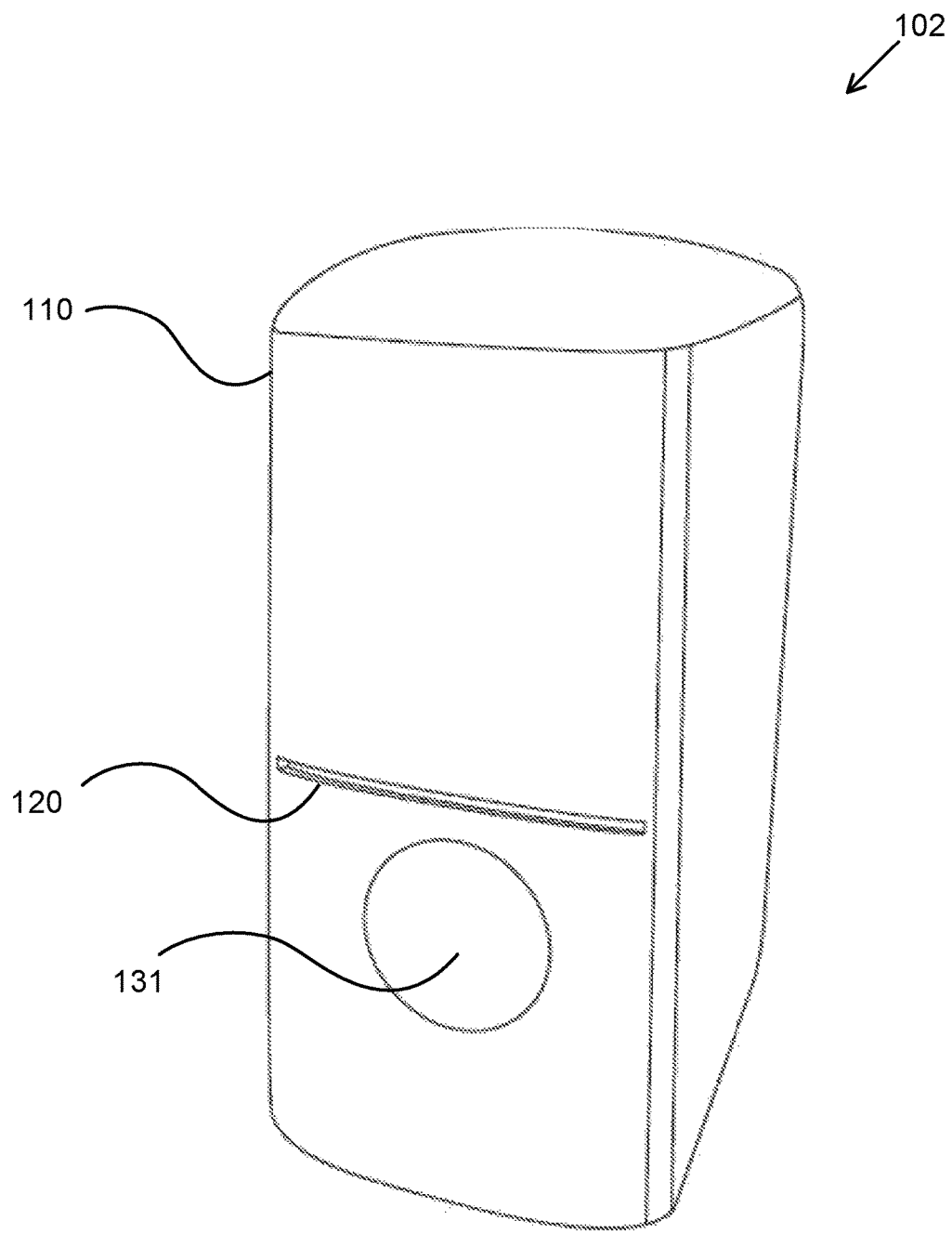
FIG. 18 is a front view of a barrier dispenser in accordance with another embodiment.

Next, the user may slide the stethoscope head with the film from the first lobe 132-1 to the center 132-0 of the recess (see FIG. 8F), and remove the stethoscope head from the recess with the film wrapped around the stethoscope head with a hand (or gloved hand) using their fingertips (e.g., thumb, index finger, middle finger). The dispenser may be configured to be used by any user, independent of whether the user is right or left-handed. The user may then pull the stethoscope head and the film downwards until the stethoscope head is below the cutting edge 140, as shown in FIG. 15. Once there is sufficient clearance, the user may cut the film with the cutting edge or by tearing perforations in the film, to release the wrapped stethoscope head, as shown in FIGS. 16A and 16B. In some cases, any excess film or loose hanging flaps 154 of the film can be tucked by the user and wrapped around an upper portion of the stethoscope head prior to use. The film that is wrapped around the stethoscope head constitutes as a protective barrier 152 as described elsewhere herein. FIG. 17 shows the barrier 152 as applied to the stethoscope head, with the excess film 154 tucked in by the user's fingers. The barrier may be formed as a smooth layer covering a distal surface 164 of the stethoscope head 160. The barrier may be formed with few or no creases (airgaps) between the film and the distal surface of the stethoscope head. The barrier may be formed without the user contacting the distal surface of the stethoscope head. The barrier may also be formed without the user contacting any part of the film/barrier that is applied to the distal surface of the stethoscope head. This can help to reduce contamination and risk of infection to both the user (e.g., healthcare personnel) and the patients. The barrier may be disposable and configured for a single use or patient encounter. FIG. 18 is a front view of a barrier dispenser in accordance with another embodiment. The dispenser 102 is similar to the dispenser 100 described elsewhere herein except for the following differences. In FIG. 18, a recess 131 of the dispenser 102 may have a substantially circular shape instead of a triangular shape. The recess 131 may be sized to receive a variety of types of stethoscope heads. For example, a dimension (e.g. diameter) of the recess may be at least 5%, 10%, 15%, 20%, 25%, 30%, 35%, 40%, 45%, or 50% greater than a dimension (e.g. diameter) of a stethoscope head. As shown in FIG. 18, the cutting edge may be optionally omitted, for example when the source of film is provided as separate sheets, individual sheets, or when the source of film includes perforations that allow sheets of film to be easily and manually separated by the user by hand.

Figure 19:
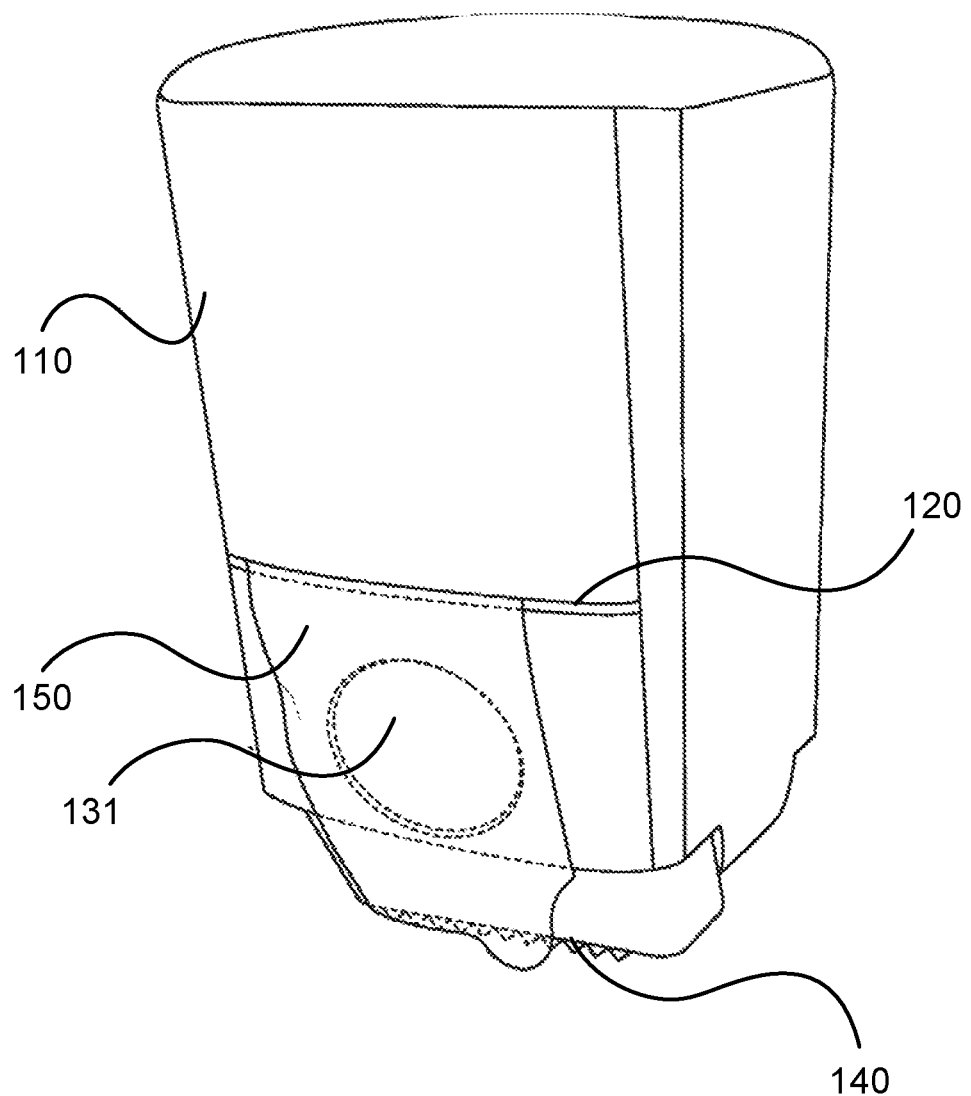
FIG. 19 is a front view of a barrier dispenser showing a film hanging in proximity to a substantially circular-shaped recess.

FIG. 19 is a front view of a barrier dispenser showing a film hanging in proximity to a substantially circular-shaped recess. The film 150 may be dispensed from the opening 120 such that it hangs or drapes over the recess 131. The extended portion of the film may completely cover the recess. In some cases, the film need not completely cover the recess, and may leave one or more portions of the recess exposed. A width of the film may be greater than, equal to, or less than the diameter of the recess. For example, in FIG. 19, the width of the film may be greater than the diameter of the recess although the invention is not limited thereto. In some cases, the width of the film may be equal or less than the diameter of the recess. In the example of FIG. 19, a cutting edge 140 may be optionally included with the dispenser.

Figure 20:
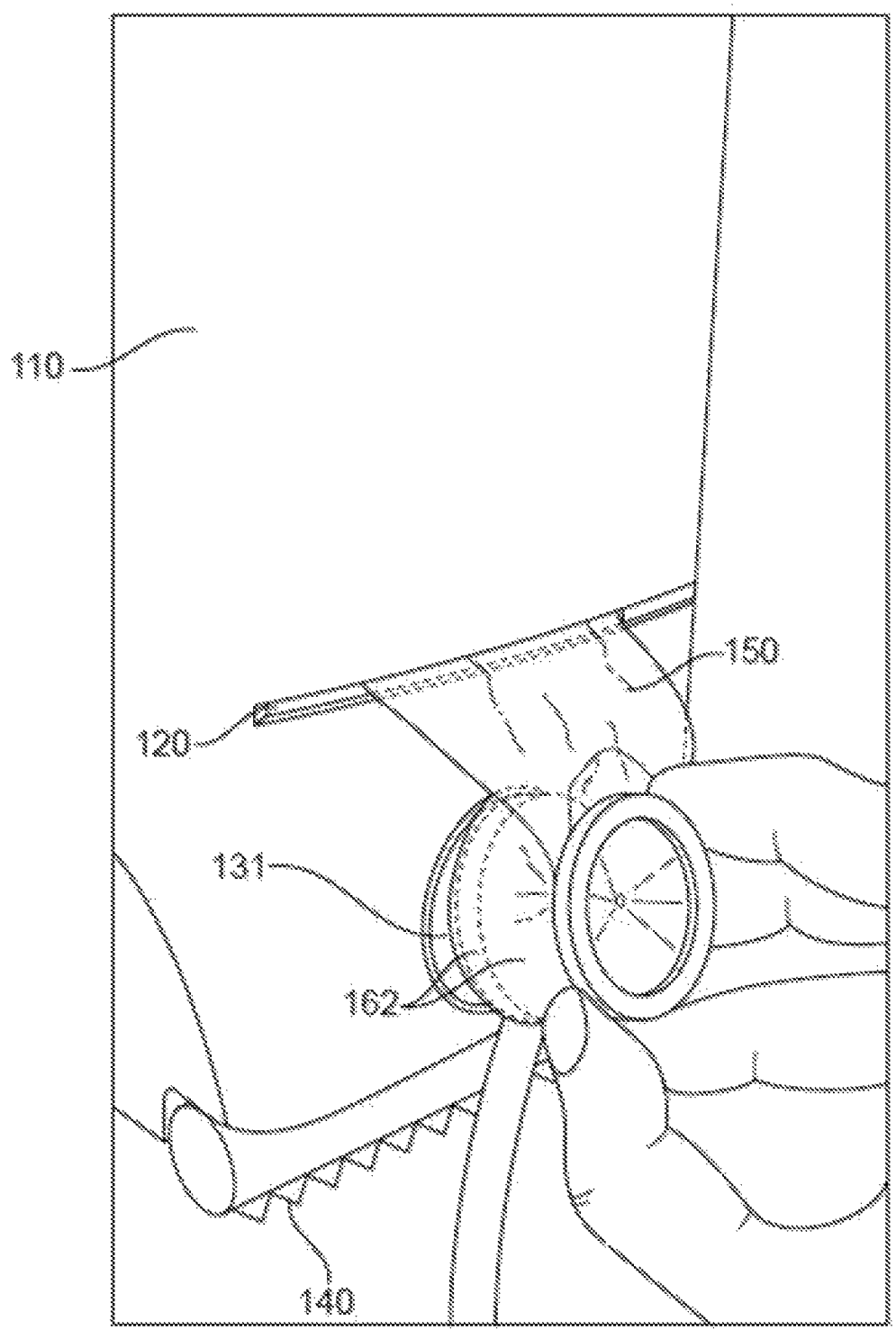
FIG. 20 is a perspective view showing a barrier being applied to a stethoscope head using the dispenser of FIG. 19.

FIG. 20 is a perspective view showing a barrier being applied to a stethoscope head using the dispenser of FIG. 19. A user may place the stethoscope head 160 onto a portion of the film 150 in front of the recess 131. Next, the user may push the stethoscope head with the film into the recess, with the film located in-between the stethoscope head and the recess. The stethoscope head may be placed, for example at or near the center of the recess. The film may be applied onto a distal surface of the stethoscope head when the user pushes the stethoscope head against the bottom surface of the recess. The film may easily attach to the stethoscope head such that light compression of the film causes the film to stick to the stethoscope head. The user may move the stethoscope head with the film within the recess, for example by rotating in a clockwise or counterclockwise manner in order to wrap the film around an edge portion 162 of the stethoscope head in one continuous sweeping motion, or with multiple smaller clockwise or counter clockwise sweeping directions. The stethoscope head with the film may be rotated by an angle within the recess ranging from about 10 degrees to about 360 degrees. In some cases, the user may simply push the stethoscope head with the film into the recess, and tuck any excess film around an upper portion of the stethoscope head, without any rotation of the stethoscope head in the recess.

After the film is wrapped around the stethoscope head to form a barrier, using the fingertips of the hand, the user may remove the stethoscope head with the film from the recess. The user may then pull the stethoscope head and the film downwards until the stethoscope head is below the cutting edge 140, for example as previously described with reference to FIG. 15. Once there is sufficient clearance, the user may cut the film to release the stethoscope head with the applied barrier, as previously described reference to FIGS. 16A and 16B. In some cases, any excess film or loose hanging flaps of the film can be tucked by the user and wrapped around an upper portion of the stethoscope head prior to use. The film that is wrapped around the stethoscope head constitutes as a protective barrier as described elsewhere herein. As previously described, no cutter or cutting may be necessary if the film comprises perforated film, or if interleaved stacked sheets or a cassette is used instead of a roll of film.

Figure 21:
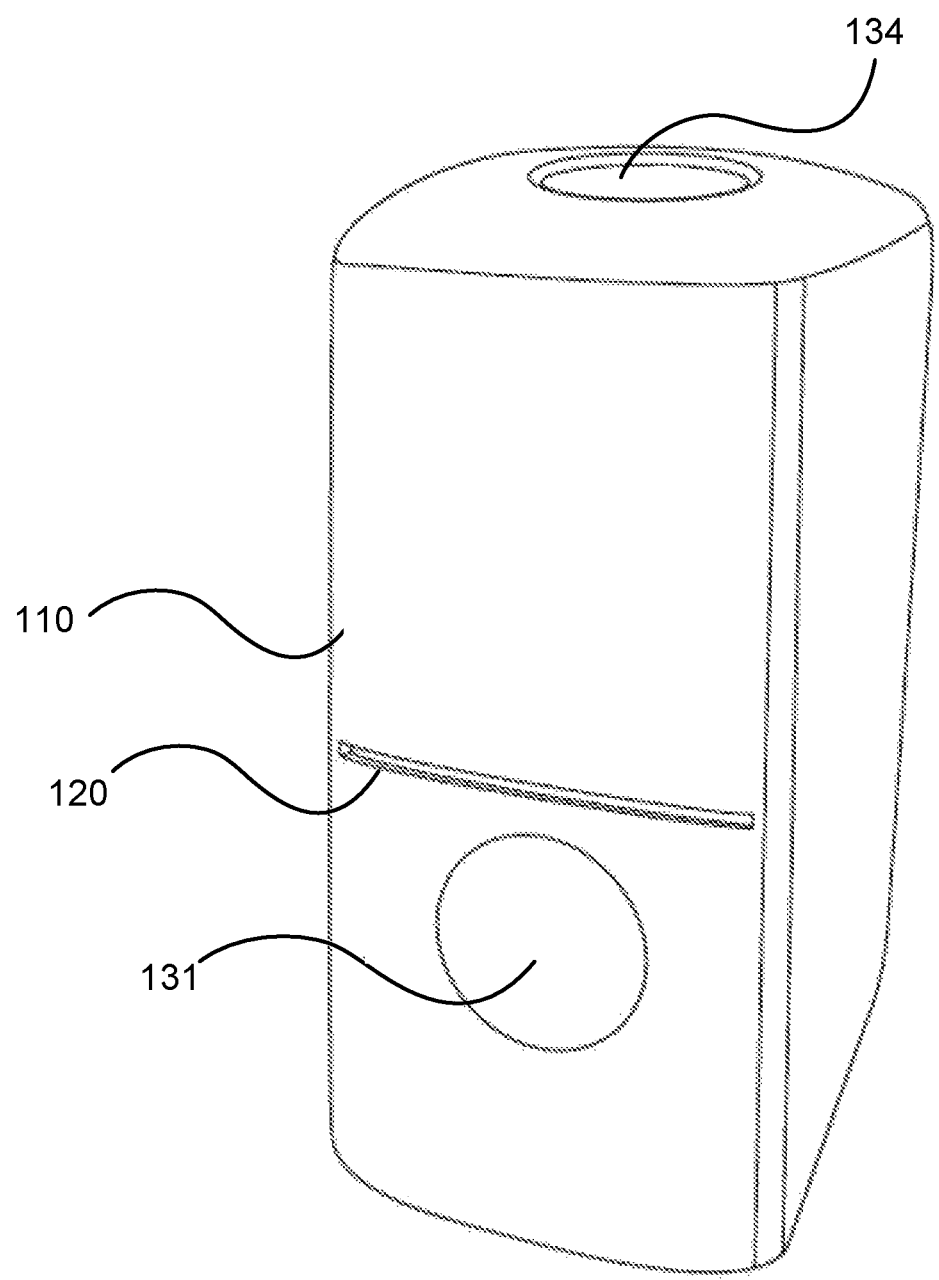
FIGS. 21 and 22 are perspective views showing a recess for flattening or smoothing the film after it has been applied to the stethoscope head.
Figure 22:
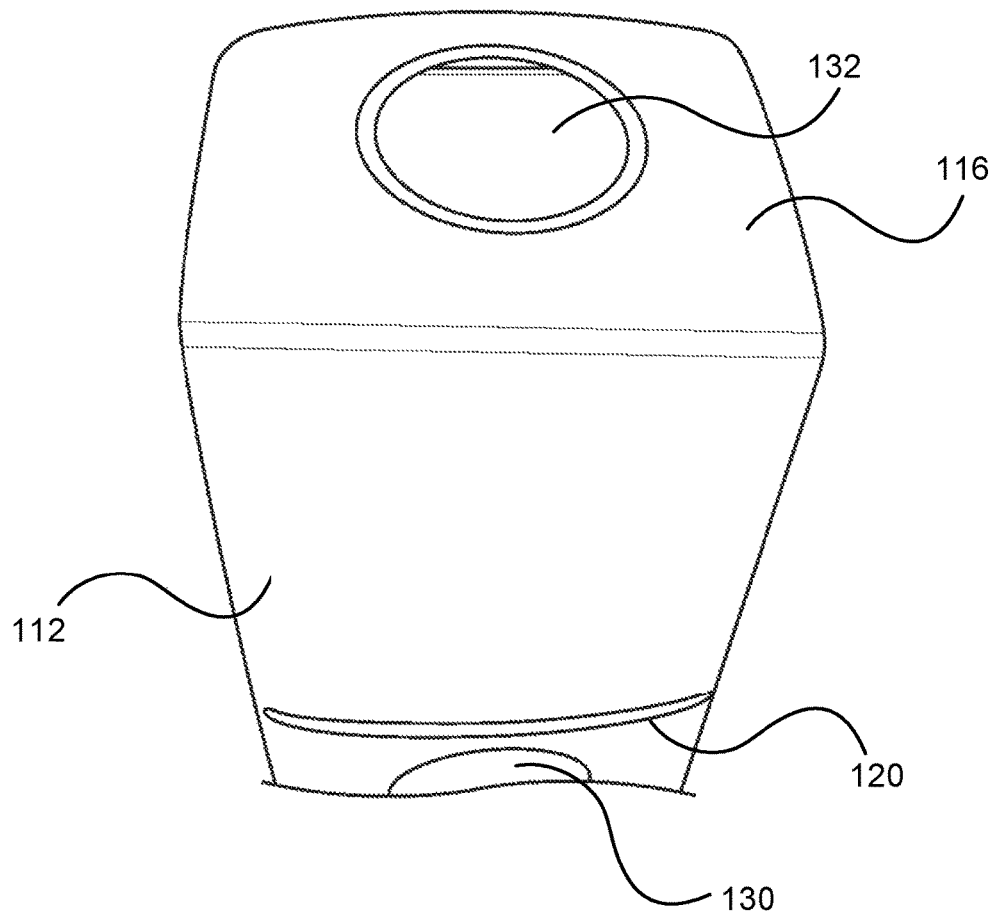

Optionally in any of the embodiments disclosed herein, the dispenser may further include one or more areas for flattening or smoothing the film after it has been applied to the stethoscope head. For example, referring to FIGS. 21 and 22, a recess 134 may be provided on a top portion of the housing 110, in addition to the recess 131 (or recess 130) on the front portion of the housing. The recess 130/131 can be used for applying the film to the stethoscope head to form a barrier as described elsewhere herein and may be employed in any of the dispensers described herein. The recess 134 can be used for flattening or smoothing the film/barrier after it has been applied to the stethoscope head. Optionally in any of the embodiments disclosed herein, the recess 134 may include an anti-microbial material for disinfecting or sterilizing the stethoscope head before and/or after patient use. The anti-microbial material may be a liquid or gel-like material that is coated onto the barrier. Optionally in any of the embodiments disclosed herein, an energy source (e.g., an ultraviolet illumination source) for reducing the amount of microorganisms, disease, virus, cellular, or bacteria on the stethoscope head and the barrier may be provided in the recess 134. Additional details about the energy source are described elsewhere herein, for example with reference to FIG. 24.

Figure 23A:
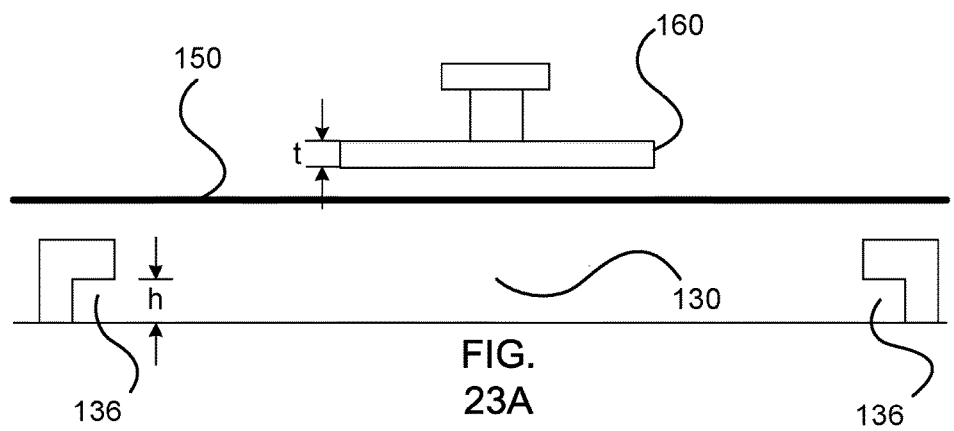
FIGS. 23A through 23C are schematic cross-sectional views showing a recess comprising an undercut region, and an exemplary method of applying the film to the stethoscope head with aid of the undercut regions to form the barrier.
Figure 23B:
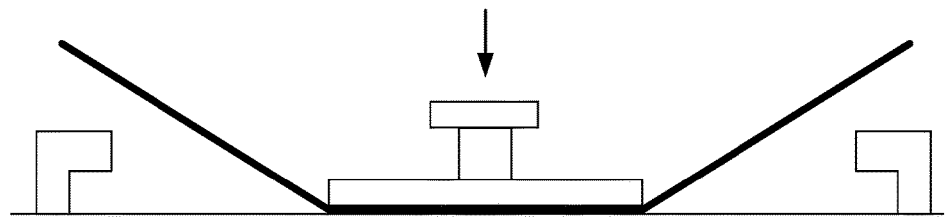
Figure 23C:
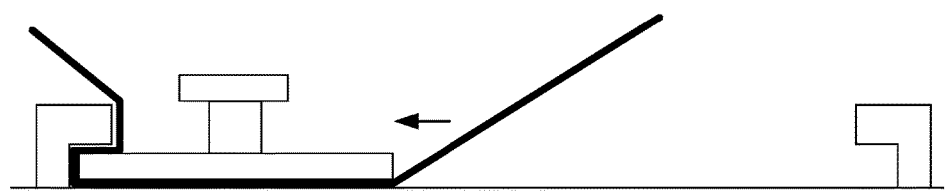

Optionally in any of the embodiments of dispensers disclosed herein, the dispenser may include a recess comprising an undercut region. The undercut region may extend along a periphery of the recess. In some cases, the undercut region may be provided at the corners of the recess (e.g. at the rounded concave lobes). FIG. 23A is a schematic cross-sectional view of a recess 130 comprising one or more undercut regions 136 in accordance with any of the embodiments disclosed herein. FIGS. 23A through 23C additionally show a stethoscope head 160 and film 150 being placed into the recess and moved to an undercut region, thereby causing the film to wrap partially around an edge portion of the stethoscope head to form a barrier. A height h of the undercut region may be configured based on a thickness profile of the stethoscope head. A distal portion of the stethoscope head may have a thickness t. The distal portion of the stethoscope head may be substantially planar. In some cases (not shown), the distal portion of the stethoscope head may have a slight curvature (e.g., slight convex). The height h of the undercut region may be greater than the thickness t of the stethoscope head in order to provide a gap when an edge portion of the stethoscope head is moved into the undercut region. The height h may be greater than the thickness t by at least about 5%, 10%, 15%, or 20%. The gap may be sized based on a thickness of the film to be applied to the stethoscope head. The film may abut against the surface of the undercut region and the stethoscope head when the edge portion of the stethoscope head is moved to the undercut region. As shown in FIG. 23C, translating the edge portion of the stethoscope head into the undercut region within the recess can cause the film to wrap around the edge portion of the stethoscope head. This is advantageous in improving adhesion of the film to the stethoscope head since the film can be wrapped around different edge portions of the stethoscope head, for example by moving the stethoscope head in a sequential manner between the undercut regions of rounded concave lobes.

Figure 24:
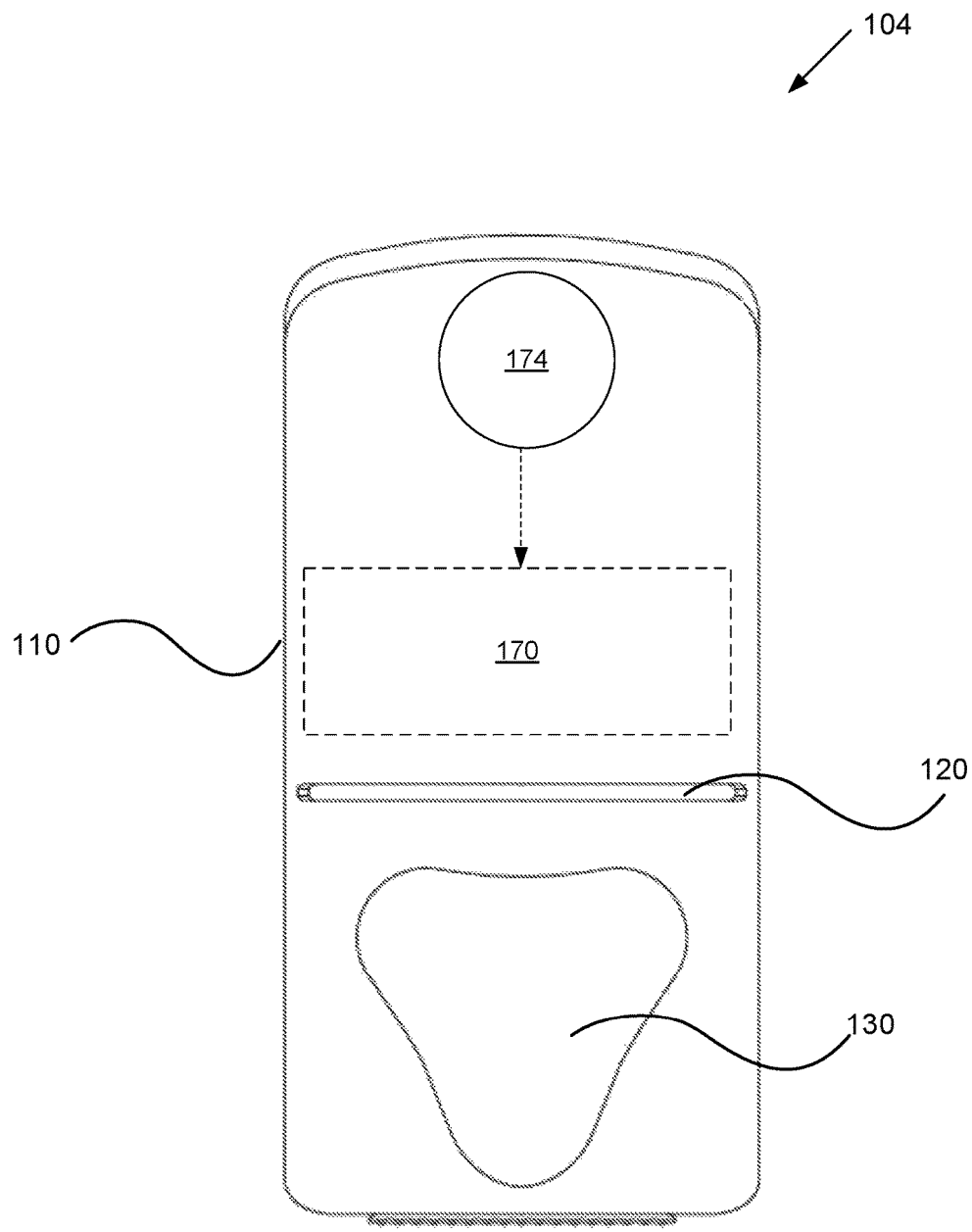
FIG. 24 is a perspective view of a barrier dispenser comprising an energy source, in accordance with an embodiment.

FIG. 24 is a perspective view of a barrier dispenser comprising an energy source, in accordance with any of the embodiments disclosed herein. The dispenser 104 may include an energy source 170. The energy source can be disposed within the chamber of the housing as described in one or more embodiments elsewhere herein. The energy source 170 may be powered by a power supply 174. FIG. 24 shows the power supply located onboard the dispenser although the invention is not limited thereto. In any of the embodiments disclosed herein, the power supply may be located remotely to the dispenser.

The energy source 170 can be configured to illuminate the stethoscope head for disinfecting or sterilizing the stethoscope head, that can apply to any of the embodiments disclosed herein. The energy source may be configured to emit one or more wavelengths of light that can kill microorganisms, disease, virus, cellular, or bacteria on the stethoscope head. The energy source may include, for example an antimicrobial ultraviolet (UV/UV-C) light source. The energy source may include, for example one or more UV light emitting diodes (LEDs). The energy source may include a germicidal lamp. The illumination by the energy source can be used to help control the level of microorganisms, disease, virus, cellular, or bacteria on the stethoscope head present on and around the stethoscope head and film/barrier. Most common microorganisms, disease, virus, cellular, or bacteria organisms that can cause sickness and disease in humans can be killed with moderate doses of ultraviolet light having a wavelength between about 260 nm and about 280 nm. Accordingly, the energy source may be configured to emit ultraviolet light having a wavelength between about 260 nm and about 280 nm, up to 350 nm. The UV light may be pulsed or continuous.

The energy source 170 may be powered by the power supply 174. The power supply may include external power, one or more batteries, solar power means, light power means, capacitors or any other energy storage device. In any of the embodiments described herein, the energy source 170 may comprise a UV light source comprising one or more UV-LEDs. The power supply 174 may comprise a solar panel configured to power the UV light source. The solar panel may comprise one or more solar energy cells. The solar panel can be mounted on the dispenser, for example on a front, side or top portion of the housing 110. The solar panel can be mounted to for optimal exposure to sunlight or other forms of electromagnetic radiation. The solar panel may include monocrystalline silicon or any other semiconductor materials for harnessing solar energy. In some cases, the solar panel may be configured to output power, for example 0.2 W or higher. The solar panel can be configured to provide any power output, depending on the size of the chamber, the amount or thickness of the barrier material to be irradiated, the type of barrier material, etc. The solar panel may be formed having any shape, size and/or design to match the housing, and can be located on a portion of the housing that does not interfere with the barrier dispensing operation of the dispenser or the operation of the solar panel.

The energy source may be activated by a switch, automatically triggered when film is advanced, or continuously exposing the barrier supply to UV/UV-C. For example, a user may turn on the switch to power on the energy source to disinfect the stethoscope head and the film/barrier, or automatically triggered when film is advanced. Alternatively, the energy source may be configured to automatically power on when the stethoscope head and the film/barrier are brought into proximity to the energy source. The energy source may also remain on all the time, or periodically through use or by timer.

Optionally in any of the embodiments disclosed herein, the energy source may be mounted to an outer surface of the housing 110 such that the energy source can illuminate ultraviolet light onto the stethoscope head and the film/barrier, after the film has been dispensed from the dispenser and applied to the stethoscope head. This configuration may permit the stethoscope head and the applied barrier to be treated with the ultraviolet light immediately prior to use with a patient.

Optionally in any of the embodiments disclosed herein, the housing 110 may include a cavity configured to support the energy source therein. An opening (for example, any of recesses 130, 131 and 134) may be provided, through which the stethoscope head and the applied barrier can be inserted into the cavity to help control the level of microorganisms, disease, virus, cellular, or bacteria on the stethoscope head present on and around the stethoscope head and film/barrier using the energy source.

Optionally in any of the embodiments disclosed herein, the stethoscope head and the film/barrier may be made of substantially ultraviolet light-resistant materials, to prevent degradation of the stethoscope head and the film as a result of the UV/UV-C illumination. Examples of UV/UV-C light-resistant materials can include glasses, metals, silicones, and ultraviolet light resistant polymers.

Optionally in any of the embodiments disclosed herein, the energy source may be configured to emit one or more wavelengths of light for curing the film after the film has been applied to the stethoscope head to form the barrier. The curing of the film can help to improve the adhesion of the film to the stethoscope head, and prevent the film from peeling off during use. The one or more wavelengths may include infrared light, for example that provides heat to cure the film.

Figure 25:
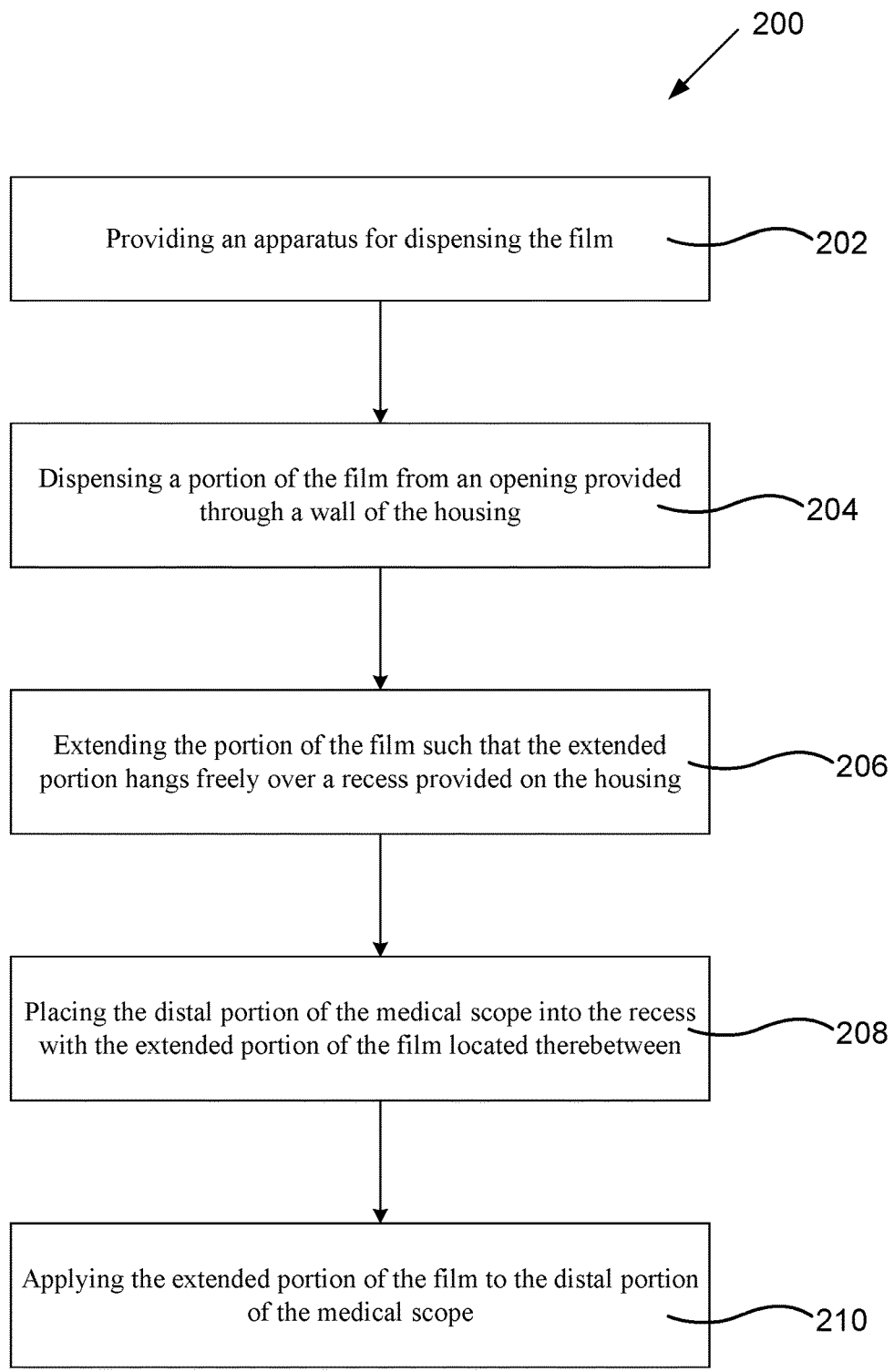
FIG. 25 is a flowchart illustrating a method of dispensing a film for use with a medical scope, in accordance with an embodiment.

FIG. 25 is a flowchart illustrating a method 200 for dispensing a film for use with a medical scope, that may apply to any of the embodiments disclosed herein. The method may be performed by one or more users, for example healthcare personnel in one or more medical environments as described elsewhere herein. The method can be used to apply a film onto a medical scope to form a protective barrier. An apparatus may include a chamber configured to receive and support therein a source of film. The method may include providing 202 an apparatus for dispensing the film; dispensing 204 a portion of the film from an opening provided through a wall of the housing; extending 206 the portion of the film such that the extended portion hangs freely over a recess provided on the housing, wherein the recess is sized to receive a distal portion of the medical scope; placing 208 the distal portion of the medical scope into the recess with the extended portion of the film located therebetween; and applying 210 the extended portion of the film to the distal portion of the medical scope.

Applying the extended portion of the film may comprise moving the distal portion of the medical scope in a translational and/or rotational manner within the recess thereby engaging the extended portion of the film with the medical scope. For example, the distal portion of the medical scope may be translated and/or rotated along a periphery of the recess. Applying the extended portion of the film may also comprise conforming or wrapping the extended portion of the film around the distal portion of the medical scope.

Optionally in any of the embodiments disclosed herein, the recess may be in the shape of a polygon. The polygon may comprise a triangle such that the recess has a substantially triangular shape. Each corner of the recess may have a radius and/or comprise a rounded concave lobe. Applying the extended portion of the film may comprise moving the distal portion of the medical scope within the recess between the corners and/or the rounded concave lobes, so as to cause the extended portion of the film to conform to or wrap around the distal portion of the medical scope. For example, the aforementioned step may comprise sliding the distal portion of the medical scope in a smooth manner between the corners and/or the rounded concave lobes within the recess. The aforementioned step may also comprise sliding the distal portion of the medical scope sequentially between the corners and/or the rounded concave lobes within the recess in a clockwise or counter-clockwise direction. Applying the extended portion of the film may comprise pressing the distal portion of the medical scope against the extended portion of the film onto a bottom of the recess. Optionally in any of the embodiments disclosed herein, the distal portion of the medical scope may be moved collectively with the extended portion of the film within the recess, so as to wrap the extended portion of the film around the distal portion of the medical scope.

Optionally in any of the embodiments disclosed herein, the method 200 may further include cutting and releasing the extended portion of the film after applying the extended portion of the film to the distal portion of the medical scope. The extended portion of the film can be cut and released using a cutting edge on the housing.

Optionally in any of the embodiments disclosed herein, the step of cutting and releasing the film can be omitted. For example, a roll comprising the film may be segmented into a plurality of pieces coupled together by perforations. The perforations may allow each piece to be manually separated from the rest of the roll for a single use with the medical scope. Accordingly, the method 200 may further include manually separating each piece along the perforations after applying the portion of the film to the distal portion of the medical scope.

Optionally in any of the embodiments disclosed herein, applying the extended portion of the film may further comprise flattening or smoothing the extended portion of the film using one or more areas of the housing.

Optionally in any of the embodiments disclosed herein, the method 200 may further comprise disinfecting or sterilizing the distal portion of the medical scope using antimicrobial, antiviral, antipathogenic, or antibacterial material provided in the film. The antimicrobial, antiviral, antipathogenic, or antibacterial material may also be provided on one or more portions of the housing, for example in one or more recesses of the housing.

Optionally in any of the embodiments disclosed herein, the method 200 may further comprise illuminating the distal portion of the medical scope with an energy source thereby disinfecting the distal portion of the medical scope. The energy source may be configured to emit ultraviolet (UV/UV-C) light as described elsewhere herein.

Optionally in any of the embodiments disclosed herein, the method 200 may further comprise curing the extended portion of film using an energy source after applying the extended portion of the film to the distal portion of the medical scope, so as to improve an adhesion strength of the film.

One or more of the previously-described embodiments, for example application of the barrier to the stethoscope head (see, e.g. FIGS. 10-17 and 20), can be easily performed using gloved hands (partial or fully gloved) or bare hands, while ensuring that a protective barrier can be properly applied to the stethoscope head. As previously described, the barrier can be used to reduce or eliminate contamination to a stethoscope head or drum. The barrier can be used to reduce the risk of microbial, bacterial, viral, disease, or pathogenic transmissions between patients and/or users. The barrier can be an antimicrobial, antiviral, antipathogenic, or antibacterial barrier. The barrier can serve as an antimicrobial, antiviral, antipathogenic, or antibacterial barrier for the stethoscope head. The barrier may include an antimicrobial, antiviral, antipathogenic, or antibacterial substance that can neutralize or destroy microbes, organic matter, contain disinfectants, metals, or a combination of both. The barrier can help to reduce or eliminate contamination of the stethoscope head when the stethoscope is being used on multiple patients. The risk of hospital-acquired infections (HAIs) to patients and users (e.g. healthcare personnel) can be significantly reduced, through use of the protective barrier applied using the apparatus and methods described herein.

Although certain embodiments and examples are provided in the foregoing description, the inventive subject matter extends beyond the specifically disclosed embodiments to other alternative embodiments and/or uses, and to modifications and equivalents thereof. For example, the apparatus and methods described herein can be applied to any type of object (other than stethoscopes) that requires a protective barrier to be applied in a reliable, quick and efficient manner. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

As used herein A and/or B encompasses one or more of A or B, and combinations thereof such as A and B. It will be understood that although the terms "first," "second," "third" etc. may be used herein to describe various elements, components, regions and/or sections, these elements, components, regions and/or sections should not be limited by these terms. These terms are merely used to distinguish one element, component, region or section from another element, component, region or section. Thus, a first element, component, region or section discussed below could be termed a second element, component, region or section without departing from the teachings of the present disclosure.

The terminology used herein is for the purpose of describing particular embodiments only and is not intended to limit the present disclosure. As used herein, the singular forms "a", "an" and "the" are intended to include the plural forms as well, unless the context clearly indicates otherwise. It will be further understood that the terms "comprises" and/or "comprising," or "includes" and/or "including," when used in this specification, specify the presence of stated features, regions, integers, steps, operations, elements and/or components, but do not preclude the presence or addition of one or more other features, regions, integers, steps, operations, elements, components and/or groups thereof.

Furthermore, relative terms, such as "lower" or "bottom" and "upper" or "top" may be used herein to describe one element's relationship to other elements as illustrated in the figures. It will be understood that relative terms are intended to encompass different orientations of the elements in addition to the orientation depicted in the figures. For example, if the element in one of the figures is turned over, elements described as being on the "lower" side of other elements would then be oriented on the "upper" side of the other elements. The exemplary term "lower" can, therefore, encompass both an orientation of "lower" and "upper," depending upon the particular orientation of the figure. Similarly, if the element in one of the figures were turned over, elements described as "below" or "beneath" other elements would then be oriented "above" the other elements. The exemplary terms "below" or "beneath" can, therefore, encompass both an orientation of above and below.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the described embodiments will be apparent to a person skilled in the art. It is therefore contemplated that the invention shall also cover any such modifications, variations and equivalents.

What is claimed is:

1. A method for dispensing a film for use with a medical scope, comprising:
    providing an apparatus for dispensing the film, wherein said apparatus comprises a chamber configured to receive and support therein a source of film;
    dispensing a portion of the film from an opening provided through a wall of the housing;
    extending the portion of the film such that the extended portion hangs freely over a recess provided on the housing, wherein the recess is sized to receive a distal portion of the medical scope;
    placing the distal portion of the medical scope into the recess with the extended portion of the film located therebetween; and
    applying the extended portion of the film to the distal portion of the medical scope, by translating and rotating the distal portion of the medical scope along a periphery of the recess in a clockwise or counter-clockwise direction, wherein the film is wrapped over an upper circumferential edge of the medical scope.

2. The method of claim 1, wherein applying the extended portion of the film comprises moving the distal portion of the medical scope in a translational and/or rotational manner within the recess thereby engaging the extended portion of the film with the medical scope.

3. The method of claim 1, wherein applying the extended portion of the film comprises translating and/or rotating the distal portion of the medical scope along a periphery of the recess.

4. The method of claim 1, wherein applying the extended portion of the film comprises conforming or wrapping the extended portion of the film around the distal portion of the medical scope.

5. The method of claim 1, further comprising illuminating the distal portion of the medical scope with energy source thereby disinfecting the distal portion of the medical scope.

6. The method of claim 1, wherein applying the extended portion of the film comprises flattening or smoothing the extended portion of the film using one or more areas of the housing.

7. The method of claim 1, wherein said method is performed in a healthcare environment.

8. The method of claim 1, further comprising disinfecting or sterilizing the distal portion of the medical scope using an anti-microbial material provided in the film.

9. The method of claim 1, wherein the recess is in the shape of a polygon.

10. The method of claim 9, wherein the polygon comprises a triangle such that the recess has a substantially triangular shape.

11. The method of claim 10, wherein each corner of the recess has a radius and/or comprises a rounded concave lobe.

12. The method of claim 11, wherein applying the extended portion of the film comprises moving the distal portion of the medical scope within the recess between the corners and/or the rounded concave lobes, so as to cause the extended portion of the film to conform or wrap around the distal portion of the medical scope.

13. The method of claim 12, comprising sliding the distal portion of the medical scope in a smooth manner between the corners and/or the rounded concave lobes within the recess.

14. The method of claim 12, comprising sliding the distal portion of the medical scope sequentially between the corners and/or the rounded concave lobes within the recess in the clockwise or counter-clockwise direction.

15. The method of claim 1, wherein applying the extended portion of the film comprises pressing the distal portion of the medical scope against the extended portion of the film onto a bottom of the recess.

16. The method of claim 15, further comprising moving the distal portion of the medical scope with the extended portion of the film within the recess, so as to wrap the extended portion of the film around the distal portion of the medical scope.

17. The method of claim 1, further comprising cutting and releasing the extended portion of the film after applying the extended portion of the film to the distal portion of the medical scope.

18. The method of claim 17, wherein the extended portion of the film is cut and released using a cutting edge on the housing.

19. The method of claim 1, wherein the roll comprising the film is segmented into a plurality of pieces coupled together by perforations, wherein the perforations allow each piece to be manually separated from the rest of the roll for a single use with the medical scope.

20. The method of claim 19, further comprising manually separating each piece along the perforations after applying the portion of the film to the distal portion of the medical scope.

* * * * *